United States Patent
Jensen

(10) Patent No.: US 10,246,513 B2
(45) Date of Patent: Apr. 2, 2019

(54) ANTIBODIES, COMPOUNDS AND DERIVATIVES THEREOF FOR USE IN THE TREATMENT OF MALE INFERTILITY

(71) Applicant: Rigshospitalet Copenhagen University Hospital, Copenhagen Ø (DK)

(72) Inventor: Martin Blomberg Jensen, Copenhagen Ø (DK)

(73) Assignee: RIGSHOSPITALET COPENHAGEN UNIVERSITY HOSPITAL, Copenhagen Ø (DK)

(*) Notice: Subject to any disclaimer, the term of this patent is extended or adjusted under 35 U.S.C. 154(b) by 67 days.

(21) Appl. No.: 14/909,701

(22) PCT Filed: Aug. 4, 2014

(86) PCT No.: PCT/DK2014/050235
§ 371 (c)(1),
(2) Date: Feb. 2, 2016

(87) PCT Pub. No.: WO2015/018421
PCT Pub. Date: Feb. 12, 2015

(65) Prior Publication Data
US 2016/0168252 A1    Jun. 16, 2016

(30) Foreign Application Priority Data
Aug. 7, 2013 (EP) .................................. 13179609

(51) Int. Cl.
| A61K 39/00 | (2006.01) |
| C07K 16/00 | (2006.01) |
| A61K 38/00 | (2006.01) |
| C07K 16/28 | (2006.01) |
| A61K 39/395 | (2006.01) |
| A61K 38/17 | (2006.01) |

(52) U.S. Cl.
CPC ...... C07K 16/2875 (2013.01); A61K 38/1793 (2013.01); A61K 39/395 (2013.01); A61K 2039/505 (2013.01); C07K 2317/21 (2013.01); C07K 2317/76 (2013.01)

(58) Field of Classification Search
None
See application file for complete search history.

(56) References Cited

U.S. PATENT DOCUMENTS

| 4,357,934 A * | 11/1982 | Fahim .................... A61D 19/00 514/179 |
| 4,411,993 A | 10/1983 | Gillis |
| 4,703,004 A | 10/1987 | Hopp et al. |
| 4,816,567 A | 3/1989 | Cabilly et al. |
| 4,946,778 A | 8/1990 | Ladner et al. |
| 5,260,203 A | 11/1993 | Ladner et al. |
| 2002/0150534 A1 * | 10/2002 | Yu ........................ A61K 31/713 424/1.49 |
| 2003/0021785 A1 | 1/2003 | Dougall |
| 2003/0148466 A1 * | 8/2003 | Fox ........................ C07K 14/47 435/69.5 |
| 2004/0033535 A1 | 2/2004 | Boyle et al. |
| 2006/0194280 A1 * | 8/2006 | Dillon .............. A61K 39/39525 435/69.1 |
| 2007/0281906 A1 | 12/2007 | Dalton et al. |
| 2008/0107597 A1 * | 5/2008 | Boyle .............. A61K 47/48546 424/1.49 |

FOREIGN PATENT DOCUMENTS

| EP | 0 911 342 B1 | 5/2006 |
| EP | 1 257 648 B1 | 6/2008 |
| EP | 0 951 551 B1 | 7/2008 |
| EP | 1 409 016 B1 | 4/2010 |
| WO | WO 88/01649 A1 | 3/1988 |
| WO | WO 2007/020042 A1 | 2/2007 |
| WO | WO 2007/080404 A2 | 7/2007 |
| WO | WO 2010/017051 A1 | 2/2010 |
| WO | WO 2010/022120 A1 | 2/2010 |
| WO | WO 2012/031118 A2 | 3/2012 |
| WO | WO 2013/067639 A1 | 5/2013 |

OTHER PUBLICATIONS

Shahmanesh et al. Antispermatozoal antibodies in men with urethritis. Fertility and Sterility, vol. 46, No. 2 (Aug. 1986).*
Jiang et al. Effect of Chinese Herbal Medicine on Male Infertility. Abstract. International Review of Neurobiology, vol. 135, pp. 297-311; 2017. (Year: 2017).*
Rittenberg et al. Medical treatment of male infertility. Human Fertility, vol. 13(4): 208-216, Dec. 2010. (Year: 2010).*
Kondoh et al. Ejaculatory dysfunction as a cause of infertility. Abstract. Reproductive Medicine and Biology, vol. 11, No. 1; pp. 59-64, Jan. 2012. (Year: 2012).*
Tokuriki et al. Stability effects of mutations and protein evolvability. Current Opinion in Structural Biology, 19:596-604, 2009. (Year: 2009).*
Bhattacharya et al. Impact of genetic variation on three dimensional structure and function of Proteins, PLoS One 12(3):e0171355, pp. 1-22, Mar. 15, 2017. (Year: 2017).*
Jurisicova et al. DNA damage in round spermatids of mice with a targeted disruption of the Pp1cgamma gene and in testicular biopsies of patients with non-obstructive azoospermia. Molecular Human Reproduction vol. 5, No. 4, pp. 323-330 (1999). (Year: 1999).*
Lewis, S. The treatment of osbstructive azoospermia by intracytoplasmic sperm injection. Andrologie No. 1, pp. 28-39 (2006). (Year: 2006).*

(Continued)

*Primary Examiner* — Elizabeth C. Kemmerer
*Assistant Examiner* — Regina M DeBerry
(74) *Attorney, Agent, or Firm* — Knobbe, Martens, Olson & Bear LLP

(57) ABSTRACT

The present invention relates to antagonists or inhibitors, which bind selectively to RANKL/OPGbp and regulate the interaction between RANKL/OPGbp and RANK/OPG. In particular, the present invention relates to an antibody or antigen binding domain, fragment or derivative thereof, immunoreactive with a RANKL/OPGbppeptide for use in the treatment, prevention or alleviation of male infertility or reduced male fertility such as oligospermia or azospermia.

14 Claims, 12 Drawing Sheets

Specification includes a Sequence Listing.

(56) References Cited

OTHER PUBLICATIONS

Paul, W.E. Fundamental Immunology, Third Edition (textbook), "Fv Structure and Diversity in Three Dimensions" pp. 292-295; Raven Press, New York; 1993). (Year: 1993).*

Casset et al. (A peptide mimetic of an anti-CD4 monoclonal antibody by rational design. Biochem Biophys Res Comm. vol. 307:198-205; 2003) (Year: 2003).*

Holm et al. Functional mapping and single chain construction of the anti-cytokeratin 8 monoclonal antibody TS1. Mol Immunol. 2007 ; 44(6):1075-1084 (Year: 2007).*

Norian et al. Low serum osteoprotegerin levels in premenopausal infertile women with low bone density: an association of relevance? Fertility and Sterility vol. 91, No. 2, pp. 542-548;Feb. 2009. (Year: 2009).*

Holm et al. (Mol Immunol. 2007; 44(6):1075-1084) (Year: 2007).*

Beckmann, M. Patricia et al., "Monoclonal Antibodies Block Murine IL-4 Receptor Function" The Journal of Immunology, Jun. 1, 1990, pp. 4212-4217, vol. 144, No. 11.

Boulianne, Gabrielle L. et al., "Production of functional chimaeric mouse/human antibody" Nature, Dec. 13, 1984, pp. 643-646, vol. 312.

Brodeur, Bernard R. et al., "Mouse-Human Myeloma Partners for the Production of Heterohybridomas" Monoclonal Antibody Production Techniques and Applications, 1987, pp. 51-63.

Cabilly, Shmuel et al., "Generation of antibody activity from immunoglobulin polypeptide chains produced in *Escherichia coli*" Proc. Natl. Acad. Sci. USA, Jun. 1984, pp. 3273-3277, vol. 81.

Engvall, Eva et al., "Enzyme-linked immunosorbent assay (ELISA) Quantitative assay of immunoglobulin G" Immunochemistry, 1971, pp. 871-874, vol. 8.

Green, Larry L. "Antibody engineering via genetic engineering of the mouse: XenoMouse strains are a vehicle for the facile generation of therapeutic human monoclonal antibodies" Journal of Immunological Methods, 1999, pp. 11-23, vol. 231.

Jensen, Martin Blomberg et al., "Characterization of the testicular, epididymal and endocrine phenotypes in the Leuven Vdr-deficient mouse model: Targeting estrogen signaling" Molecular and Cellular Endocrinology, 2013, pp. 93-102, vol. 377.

Kearns, Ann E. et al., "Receptor Activator of Nuclear Factor $_\kappa$B Ligand and Osteoprotegerin Regulation of Bone Remodeling in Health and Disease" Endocrine Reviews, Apr. 2008, pp. 155-192, vol. 29, No. 2.

Köhler, G. et al., "Continuous cultures of fused cells secreting antibody of predefined specificity" Nature, Aug. 7, 1975, pp. 495-497, vol. 256.

Kozbor, Danuta et al., "A Human Hybrid Myeloma for Production of Human Monoclonal Antibodies" The Journal of Immunology, Dec. 1984, pp. 3001-3005, vol. 133, No. 6.

Lacey, David L. et al., "Bench to bedside: elucidation of the OPG-RANK-RANKL pathway and the development of denosumab" Nature Reviews, May 2012, pp. 401-419, vol. 11.

Lee, Sun-Kyeong et al., "1,25 (OH)$_2$ Vitamin D$_3$-Stimulated Osteoclast Formation in Spleen-Osteoblast Cocultures Is Mediated in Part by Enhanced IL-1$\alpha$ and Receptor Activator of NF-$_\kappa$B Ligand Production in Osteoblasts" The Journal of Immunology, 2002, pp. 2374-2380, vol. 169.

Lewis, Craig M. et al., "Use of a Novel Mutagenesis Strategy, Optimized Residue Substitution, to Decrease the Off-Rate of an Anti-gp120 Antibody" Molecular Immunology, 1995, pp. 1065-1072, vol. 32, No. 14/15.

Liu, Alvin Y. et al., "Chimeric mouse-human IgGi antibody that can mediate lysis of cancer cells" Proc. Natl. Sci. USA, May 1987, pp. 3439-3443, vol. 84.

Miller, Paul D. "Denosumab: Anti-RANKL Antibody" Current Osteoporosis Reports, 2009, pp. 18-22, vol. 7.

Morrison, Sherie L. et al., "Chimeric human antibody molecules: Mouse antigen-binding domains with human constant region domains" Proc. Natl. Acad. Sci. USA, Nov. 1984, pp. 6851-6855, vol. 81.

Müller, Rolf "Determination of Affinity and Specificity of Anti-Hapten Antibodies by Competitive Radioimmunoassay" Methods in Enzymology, 1983, pp. 589-601, vol. 92.

Neuberger, M.S. et al., "A hapten-specific chimaeric IgE antibody with human physiological effector function" Nature, Mar. 1985, pp. 268-270, vol. 314.

Pazdur, Richard "FDA Approval for Denosumab" National Cancer Institute, Cancer Drug Information, Jul. 2, 2013, pp. 1-6, XP-002730881.

Prolia (denosubab)—Injection, for subcutaneous use—insert Amgen—Apr. 17, 2013.

Raz, Eyal et al., "Intradermal gene immunization: The Possible rolde of DNA uptake in the unduction of cellular immunity to viruses" Proc. Natl. Acad. Sci. USA, Sep. 1994, pp. 9519-9523, vol. 91.

Stahl, Peter J. et al., "Contemporary Management of Male Infertility" Annu. Rev. Med., 2012, pp. 525-540, vol. 63.

Wahl, Richard L. et al., "Improved Radioimaging and Tumor Localization with Monoclonal F(ab')$_2$" Journal of Nuclear Medicine, 1983, pp. 316-325, vol. 24.

Wang, Bin et al., "Gene inoculation generates immune responses against human immunodeficiency virus type 1" Proc. Natl. Acad. Sci. USA, May 1993, pp. 4156-4160, vol. 90.

Xgeva (denosumab)—injection, for subcutaneous use—insert Amgen—Apr. 17, 2013.

International Search Report for PCT/DK2014/050235 dated Nov. 3, 2014.

* cited by examiner

SEQUENCE LISTING

<160> NUMBER OF SEQ ID NOS: 11

<210> SEQ ID NO 1
<211> LENGTH: 1630
<212> TYPE: DNA
<213> ORGANISM: Mus musculus
<220> FEATURE:
<221> NAME/KEY: source
<222> LOCATION: 1..1630
<223> OTHER INFORMATION: /mol_type="unassigned DNA"
   /note="Full length cDNA"
   /organism="Mus musculus"

<400> SEQUENCE: 1

```
ccggcgtccc acacgagggt ccgctgcacc ccgcgccttc tgcaccggct ccggcgccgc     60
cacccgccgc ctcccgctcc atgttcctgg ccctcctggg gctgggactg ggccaggtgg    120
tctgcagcat cgctctgttc ctgtactttc gagcgcagat ggatcctaac agaatatcag    180
aagacagcac tcactgcttt tatagaatcc tgagactcca tgaaaacgca gatttgcagg    240
actcgactct ggagagtgaa gacacactac ctgactcctg caggaggatg aaacaagcct    300
ttcaggggc cgtgcagaag gaactgcaac acattgtggg gccacagcgc ttctcaggag    360
ctccagctat gatggaaggc tcatggttgg atgtggccca gcgaggcaag cctgaggccc    420
agccatttgc acacctcacc atcaatgctg ccagcatccc atcgggttcc ataaagtca    480
ctctgtcctc ttggtaccac gatcgaggct gggccaagat ctctaacatg acgttaagca    540
acggaaaact aagggttaac caagatggct tctattacct gtacgccaac atttgctttc    600
ggcatcatga acatcggga agcgtaccta cagactatct tcagctgatg gtgtatgtcg    660
ttaaaaccag catcaaaatc ccaagttctc ataacctgat gaaaggaggg agcacgaaaa    720
actggtcggg caattctgaa ttccactttt attccataaa tgttggggga ttttttcaagc    780
tccgagctgt tgaagaaatt agcattcagg tgtccaaccc ttccctgctg gatccggatc    840
aagatgcgac gtactttggg gctttcaaag ttcaggacat agactgagac tcatttcgtg    900
gaacattagc atggatgtcc tagatgtttg gaaacttctt aaaaaatgga tgatgtctat    960
acatgtgtaa gactactaag agacatggcc cacggtgtat gaaactcaca gccctctctc   1020
ttgagcctgt acaggttgtg tatatgtaaa gtccataggt gatgttagat tcatggtgat   1080
tacacaacgg ttttacaatt ttgtaatgat ttcctagaat tgaaccagat tgggagaggt   1140
attccgatgc ttatgaaaaa cttacacgtg agctatggaa gggggtcaca gtctctgggt   1200
ctaaccctg gacatgtgcc actgagaacc ttgaaattaa gaggatgcca tgtcattgca   1260
aagaaatgat agtgtgaagg gttaagttct tttgaattgt tacattgcgc tgggacctgc   1320
aaataagttc tttttttcta atgaggagag aaaaatatat gtattttat ataatgtcta   1380
aagttatatt tcaggtgtaa tgttttctgt gcaaagtttt gtaaattata tttgtgctat   1440
agtatttgat tcaaaatatt taaaaatgtc tcactgttga catatttaat gttttaaatg   1500
tacagatgta tttaactggt gcactttgta attcccctga aggtactcgt agctaagggg   1560
gcagaatact gttctggtg accacatgta gtttatttct ttattctttt taacttaata   1620
gagtcttcag                                                          1630
```

<210> SEQ ID NO 2
<211> LENGTH: 294
<212> TYPE: PRT
<213> ORGANISM: Mus musculus

<400> SEQUENCE: 2

Gly Val Pro His Glu Gly Pro Leu His Pro Ala Pro Ser Ala Pro Ala
1               5                   10                  15

Pro Ala Pro Pro Ala Ala Ser Arg Ser Met Phe Leu Ala Leu Leu
            20                  25                  30

Gly Leu Gly Leu Gly Gln Val Val Cys Ser Ile Ala Leu Phe Leu Tyr
            35                  40                  45

Phe Arg Ala Gln Met Asp Pro Asn Arg Ile Ser Glu Asp Ser Thr His
50                  55                  60

Cys Phe Tyr Arg Ile Leu Arg Leu His Glu Asn Ala Asp Leu Gln Asp
65                  70                  75                  80

Ser Thr Leu Glu Ser Glu Asp Thr Leu Pro Asp Ser Cys Arg Arg Met
                85                  90                  95

Lys Gln Ala Phe Gln Gly Ala Val Gln Lys Glu Leu Gln His Ile Val
                100                 105                 110

Gly Pro Gln Arg Phe Ser Gly Ala Pro Ala Met Met Glu Gly Ser Trp
                115                 120                 125

Leu Asp Val Ala Gln Arg Gly Lys Pro Glu Ala Gln Pro Phe Ala His
        130                 135                 140

Leu Thr Ile Asn Ala Ala Ser Ile Pro Ser Gly Ser His Lys Val Thr
145                 150                 155                 160

Leu Ser Ser Trp Tyr His Asp Arg Gly Trp Ala Lys Ile Ser Asn Met
                165                 170                 175

Thr Leu Ser Asn Gly Lys Leu Arg Val Asn Gln Asp Gly Phe Tyr Tyr
                180                 185                 190

Leu Tyr Ala Asn Ile Cys Phe Arg His His Glu Thr Ser Gly Ser Val
        195                 200                 205

Pro Thr Asp Tyr Leu Gln Leu Met Val Tyr Val Val Lys Thr Ser Ile
210                 215                 220

Lys Ile Pro Ser Ser His Asn Leu Met Lys Gly Gly Ser Thr Lys Asn
225                 230                 235                 240

Trp Ser Gly Asn Ser Glu Phe His Phe Tyr Ser Ile Asn Val Gly Gly
                245                 250                 255

Phe Phe Lys Leu Arg Ala Gly Glu Glu Ile Ser Ile Gln Val Ser Asn
                260                 265                 270

Pro Ser Leu Leu Asp Pro Asp Gln Asp Ala Thr Tyr Phe Gly Ala Phe
        275                 280                 285

Lys Val Gln Asp Ile Asp
        290

<210> SEQ ID NO 3
<211> LENGTH: 954
<212> TYPE: DNA
<213> ORGANISM: Homo sapiens
<220> FEATURE:
<221> NAME/KEY: source
<222> LOCATION: 1..954
<223> OTHER INFORMATION: /mol_type="unassigned DNA"
      /note="Full length cDNA"
      /organism="Homo sapiens"

<400> SEQUENCE: 3
atgcgccgcg ccagcagaga ctacaccaag tacctgcgtg gctcggagga gatgggcggc      60
ggccccggag ccccgcacga gggcccccctg cacgccccgc cgccgcctgc gccgcaccag     120 cccccgccg cctcccgctc catgttcgtg gccctcctgg gctgggggct gggccaggtt       180
gtctgcagcg tcgccctgtt cttctatttc agagcgcaga tggatcctaa tagaatatca     240

```
gaagatggca ctcactgcat ttatagaatt ttgagactcc atgaaaatgc agattttcaa    300
gacacaactc tggagagtca agatacaaaa ttaatacctg attcatgtag agaaattaaa    360
caggcctttc aaggagctgt gcaaaaggaa ttacaacata tcgttggatc acagcacatc    420
agagcagaga aagcgatggt ggatggctca tggttagatc tggccaagag gagcaagctt    480
gaagctcagc cttttgctca tctcactatt aatgccaccg acatcccatc tggttcccat    540
aaagtgagtc tgtcctcttg gtaccatgat cggggttggg ccaagatctc aacatgact    600 tttagcaatg gaaaactaat agttaatcag gatggctttt attacctgta tgccaacatt    660
tgctttcgac atcatgaaac ttcaggagac ctagctacag agtatcttca actaatggtg    720
tacgtcacta aaccagcat caaaatccca gttctcata ccctgatgaa aggaggaagc    780
accaagtatt ggtcagggaa ttctgaattc catttttatt ccataaacgt tggtggatt    840 tttaagttac ggtctggaga ggaaatcagc atcgaggtct ccaaccctc cttactggat    900 ccggatcagg atgcaacata ctttggggct tttaaagttc gagatataga ttga        954

<210> SEQ ID NO 4
<211> LENGTH: 317
<212> TYPE: PRT
<213> ORGANISM: Homo sapiens

<400> SEQUENCE: 4

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
```

```
                        245                 250                 255
Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
            275                 280                 285

Ile Ser Ile Glu Val Ser Asn Pro Ser Leu Leu Asp Pro Asp Gln Asp
            290                 295                 300

Ala Thr Tyr Phe Gly Ala Phe Lys Val Arg Asp Ile Asp
305                 310                 315

<210> SEQ ID NO 5
<211> LENGTH: 39
<212> TYPE: PRT
<213> ORGANISM: Homo sapiens

<400> SEQUENCE: 5

Gly Phe Tyr Tyr Leu Tyr Ala Asn Ile Cys Phe Arg His His Glu Thr
1               5                   10                  15

Ser Gly Asp Leu Ala Thr Glu Tyr Leu Gln Leu Met Val Tyr Val Thr
            20                  25                  30

Lys Thr Ser Ile Lys Ile Pro
            35

<210> SEQ ID NO 6
<211> LENGTH: 5
<212> TYPE: PRT
<213> ORGANISM: Homo sapiens

<400> SEQUENCE: 6

Asp Leu Ala Thr Glu
1               5

<210> SEQ ID NO 7
<211> LENGTH: 467
<212> TYPE: PRT
<213> ORGANISM: Homo sapiens

<400> SEQUENCE: 7

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Ser Tyr Ala Met Ser Trp Val Arg Gln Ala Pro Gly Lys Gly Leu
    50                  55                  60

Glu Trp Val Ser Gly Ile Thr Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Pro Gly Thr Thr Val Ile Met Ser Trp Phe
            115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160
```

Glu Ser Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
        195                 200                 205
Val Val Thr Val Pro Ser Ser Asn Phe Gly Thr Gln Thr Tyr Thr Cys
    210                 215                 220
Asn Val Asp His Lys Pro Ser Asn Thr Lys Val Asp Lys Thr Val Glu
225                 230                 235                 240
Arg Lys Cys Cys Val Glu Cys Pro Pro Cys Pro Ala Pro Pro Val Ala
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Gln Phe Asn Trp Tyr Val Asp Gly Val Glu Val
    290                 295                 300
His Asn Ala Lys Thr Lys Pro Arg Glu Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
            340                 345                 350
Glu Lys Thr Ile Ser Lys Thr Lys Gly Gln Pro Arg Glu Pro Gln Val
        355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 8
<211> LENGTH: 122
<212> TYPE: PRT
<213> ORGANISM: Mus musculus

<400> SEQUENCE: 8

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Gly Ile Thr Gly Ser Gly Gly Ser Thr Tyr Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser
        115                 120
```

<210> SEQ ID NO 9
<211> LENGTH: 235
<212> TYPE: PRT
<213> ORGANISM: Homo sapiens

<400> SEQUENCE: 9

```
Met Glu Thr Pro Ala Gln Leu Leu Phe Leu Leu Leu Leu Trp Leu Pro
 1               5                  10                  15

Asp Thr Thr Gly Glu Ile Val Leu Thr Gln Ser Pro Gly Thr Leu Ser
                 20                  25                  30

Leu Ser Pro Gly Glu Arg Ala Thr Leu Ser Cys Arg Ala Ser Gln Ser
             35                  40                  45

Val Arg Gly Arg Tyr Leu Ala Trp Tyr Gln Gln Lys Pro Gly Gln Ala
         50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Phe Tyr Cys Gln Gln Tyr
            100                 105                 110

Gly Ser Ser Pro Arg Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 10
<211> LENGTH: 108
<212> TYPE: PRT
<213> ORGANISM: Mus musculus

<400> SEQUENCE: 10

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Arg Gly Arg
```

```
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Phe Tyr Cys Gln Gln Tyr Gly Ser Ser Pro
                85                  90                  95
Arg Thr Phe Gly Gln Gly Thr Lys Val Glu Ile Lys
            100                 105

<210> SEQ ID NO 11
<211> LENGTH: 616
<212> TYPE: PRT
<213> ORGANISM: Homo sapiens

<400> SEQUENCE: 11

Met Ala Pro Arg Ala Arg Arg Arg Pro Leu Phe Ala Leu Leu Leu
1               5                   10                  15
Leu Cys Ala Leu Leu Ala Arg Leu Gln Val Ala Leu Gln Ile Ala Pro
            20                  25                  30
Pro Cys Thr Ser Glu Lys His Tyr Glu His Leu Gly Arg Cys Cys Asn
        35                  40                  45
Lys Cys Glu Pro Gly Lys Tyr Met Ser Ser Lys Cys Thr Thr Thr Ser
    50                  55                  60
Asp Ser Val Cys Leu Pro Cys Gly Pro Asp Glu Tyr Leu Asp Ser Trp
65                  70                  75                  80
Asn Glu Glu Asp Lys Cys Leu Leu His Lys Val Cys Asp Thr Gly Lys
                85                  90                  95
Ala Leu Val Ala Val Ala Gly Asn Ser Thr Thr Pro Arg Arg Cys
            100                 105                 110
Ala Cys Thr Ala Gly Tyr His Trp Ser Gln Asp Cys Glu Cys Cys Arg
        115                 120                 125
Arg Asn Thr Glu Cys Ala Pro Gly Leu Gly Ala Gln His Pro Leu Gln
    130                 135                 140
Leu Asn Lys Asp Thr Val Cys Lys Pro Cys Leu Ala Gly Tyr Phe Ser
145                 150                 155                 160
Asp Ala Phe Ser Ser Thr Asp Lys Cys Arg Pro Trp Thr Asn Cys Thr
                165                 170                 175
Phe Leu Gly Lys Arg Val Glu His His Gly Thr Glu Lys Ser Asp Ala
            180                 185                 190
Val Cys Ser Ser Ser Leu Pro Ala Arg Lys Pro Pro Asn Glu Pro His
        195                 200                 205
Val Tyr Leu Pro Gly Leu Ile Ile Leu Leu Leu Phe Ala Ser Val Ala
    210                 215                 220
Leu Val Ala Ala Ile Ile Phe Gly Val Cys Tyr Arg Lys Lys Gly Lys
225                 230                 235                 240
Ala Leu Thr Ala Asn Leu Trp His Trp Ile Asn Glu Ala Cys Gly Arg
                245                 250                 255
Leu Ser Gly Asp Lys Glu Ser Ser Gly Asp Ser Cys Val Ser Thr His
            260                 265                 270
Thr Ala Asn Phe Gly Gln Gln Gly Ala Cys Glu Gly Val Leu Leu Leu
        275                 280                 285
```

```
Thr Leu Glu Glu Lys Thr Phe Pro Glu Asp Met Cys Tyr Pro Asp Gln
    290                 295                 300
Gly Gly Val Cys Gln Gly Thr Cys Val Gly Gly Pro Tyr Ala Gln
305                 310                 315                 320
Gly Glu Asp Ala Arg Met Leu Ser Leu Val Ser Lys Thr Glu Ile Glu
                325                 330                 335
Glu Asp Ser Phe Arg Gln Met Pro Thr Glu Asp Glu Tyr Met Asp Arg
                340                 345                 350
Pro Ser Gln Pro Thr Asp Gln Leu Leu Phe Leu Thr Glu Pro Gly Ser
                355                 360                 365
Lys Ser Thr Pro Pro Phe Ser Glu Pro Leu Glu Val Gly Glu Asn Asp
370                 375                 380
Ser Leu Ser Gln Cys Phe Thr Gly Thr Gln Ser Thr Val Gly Ser Glu
385                 390                 395                 400
Ser Cys Asn Cys Thr Glu Pro Leu Cys Arg Thr Asp Trp Thr Pro Met
                405                 410                 415
Ser Ser Glu Asn Tyr Leu Gln Lys Glu Val Asp Ser Gly His Cys Pro
                420                 425                 430
His Trp Ala Ala Ser Pro Ser Pro Asn Trp Ala Asp Val Cys Thr Gly
                435                 440                 445
Cys Arg Asn Pro Pro Gly Glu Asp Cys Glu Pro Leu Val Gly Ser Pro
450                 455                 460
Lys Arg Gly Pro Leu Pro Gln Cys Ala Tyr Gly Met Gly Leu Pro Pro
465                 470                 475                 480
Glu Glu Glu Ala Ser Arg Thr Glu Ala Arg Asp Gln Pro Glu Asp Gly
                485                 490                 495
Ala Asp Gly Arg Leu Pro Ser Ser Ala Arg Ala Gly Ala Gly Ser Gly
                500                 505                 510
Ser Ser Pro Gly Gly Gln Ser Pro Ala Ser Gly Asn Val Thr Gly Asn
            515                 520                 525
Ser Asn Ser Thr Phe Ile Ser Ser Gly Gln Val Met Asn Phe Lys Gly
            530                 535                 540
Asp Ile Ile Val Val Tyr Val Ser Gln Thr Ser Gln Glu Gly Ala Ala
545                 550                 555                 560
Ala Ala Ala Glu Pro Met Gly Arg Pro Val Gln Glu Glu Thr Leu Ala
                565                 570                 575
Arg Arg Asp Ser Phe Ala Gly Asn Gly Pro Arg Phe Pro Asp Pro Cys
                580                 585                 590
Gly Gly Pro Glu Gly Leu Arg Glu Pro Glu Lys Ala Ser Arg Pro Val
            595                 600                 605
Gln Glu Gln Gly Gly Ala Lys Ala
    610                 615
```

ANTIBODIES, COMPOUNDS AND DERIVATIVES THEREOF FOR USE IN THE TREATMENT OF MALE INFERTILITY

CROSS REFERENCE TO RELATED APPLICATIONS

This application is a U.S. National Phase Application of PCT International Application No. PCT/DK2014/050235, filed on Aug. 4, 2014, designating the United States of America and published in the English language, which is an International Application of and claims the benefit of priority to European Patent Application No. 13179609.6, filed on Aug. 7, 2013. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-PLOUG24-003APC.txt, the date of creation of the ASCII text file is Feb. 1, 2016, and the size of the ASCII text file is 23 KB.

TECHNICAL FIELD OF THE INVENTION

The present invention relates to antagonists or inhibitors, which bind selectively to RANKL/OPGbp and regulate the interaction between RANKL/OPGbp and RANK/OPG. In particular, the present invention relates to an antibody or antigen binding domain, fragment or derivative thereof, immunoreactive with a RANKL/OPGbp peptide for use in the treatment, prevention or alleviation of male infertility or reduced male fertility such as oligospermia or azospermia.

BACKGROUND OF THE INVENTION

The receptor activator of NF-κB ligand (RANKL) system is considered important for bone homeostasis and comprises three important factors. RANKL is a transmembrane ligand that binds to a specific receptor (receptor activator of NF-κB (RANK)) on a neighbor cell that subsequently activates NFKB and regulates cellular activation through regulation of cell cycle i.e proliferation, differentiation and apoptosis. OPG is an endogenous secreted protein that binds RANKL and inhibits its signalling.

RANK/RANKL triggers a network of TRAF-mediated kinase cascades that promote osteoclast differentiation. RANKL is expressed on osteoblast cells and its receptor, Rank, on pre-osteoclastic cells. RANKL expression is stimulated by a number of factors, such as IL-1 , IL-6, IL-11, IL-17, TNF-α, vitamin D, $Ca^{2+}$, parathyroid, glucocorticoids, prostaglandin E2, and immunosuppressive drugs, and is down-regulated by TGF-α. The RANK/RANKL interaction induces differentiation and formation of multinucleated mature osteoclasts, causing bone resorption. The third protein agonist, osteoprotegerin (OPG), is also produced by osteoblasts and is known to exert an inhibitory effect on the pre-osteoclastic differentiation process. By binding to RANKL also known as osteoprotegerin binding protein (OPGbp), OPG inhibits the RANK/RANKL interaction and subsequent osteoclastogenesis. OPG is thus a very efficient anti-resorptive agent. It also serves as a decoy receptor for the tumour necrosis factor-related apoptosis-inducing ligand (TRAIL) and increases cell survival by blocking the apoptotic effects of this ligand. The fact that the overexpression of OPG in mice results in severe osteopetrosis and that OPG-null mice are osteoporotic is testimony to the physiological importance of OPG. The lack of RANK or RANKL induces osteopetrosis in mice.

Thus, the RANK/RANKL system is vital for activation of the bone resorbing cells (osteoclasts). In bone, the bone synthesizing cells (osteblasts) express RANKL that signals to RANK on the immature osteoclasts. This induces proliferation and activation of the cells they start to proliferate and resorb bone. OPG is produced by somatic cells in the bone and this production is regulated by sex hormones, TGF-B and various other substances. Today a human made recombinant antibody against RANKL, denosumab is used to treat osteoporosis as it inhibits RANKL signalling and thus causes less bone resorption in humans. RANKL signalling has only two other known additional functions in healthy humans as it is involved in lactation and immune cells.

Recently, use of RANK/RANKL antagonists for treating neuromuscular disorders, genetic myopathies and/or non-genetic myopathies and/or for regulating skeletal and cardiac muscle disuse, diseases and aging has also been disclosed (WO 2013/067639 A1).

Decreased semen quality is a major factor of male infertility. Semen quality is a measure of the ability of the semen to accomplish fertilization. Evaluation of male fertility potential is today basically conducted through semen analysis. A semen analysis evaluates certain characteristics of a male's semen and the spermatozoa contained in the semen. The most common variables measured to evaluate sperm quality are: sperm count, motility and morphology. However, there is no treatment for men with no sperm in the ejaculate or a drug that can increase sperm number today.

SUMMARY OF THE INVENTION

In biopsies with spermatogenic failure or severe testicular dysgeneis with carcinoma in situ, it seems as if the production of OPG in the peritubular cells vanishes. This indicates that it is possible to treat humans with an antagonist or inhibitor of RANKL, such as antagonistic anti-RANKL antibodies, which may influence proliferation and apoptosis in the germ cells. Therefore, antagonistic anti-RANKL antibodies, such as denosumab, may have a new indication as the treatment of men with no spermatozoa but presence of germ cells in the testis. Alternatively, the counterpart (RANKL) can be used to obtain the opposite effect male anticonception.

The present inventor has now shown that RANKL, RANK and OPG are expressed on both RNA and protein level in the human and mouse testis. The Sertoli cells express RANKL, while the germ cells express RANK and the peritubular cells express OPG. Normally, RANKL activates NFKB and activation of this pathway in the male gonad determines whether the testicular cells proliferate or undergo apoptosis in the testis. Therefore, this pathway appears to be a novel regulator of germ cell proliferation. This has been further documented in examples 3-5, which show that both specific compounds (illustrated by OPG) and specific antibodies (illustrated by denosumab) are able to affect positively semen quality.

It is an object of the invention to provide antagonists or inhibitors, such as antibodies or antigen binding domains, which regulate the interaction between RANKL and RANK, in particular antibodies or antigen binding domains, which block the interaction between RANKL and RANK and/or inhibit at least one activity of RANKL, which leads to male infertility or reduced male fertility. It is a further object of the invention to provide antibodies or antigen binding domains, fragments or derivatives thereof that may be used in the treatment, prevention or alleviation of male infertility or reduced male fertility. It is a further object of the invention to provide an antibody, or an antigen binding domain, or a fragment or variant thereof, which regulates the interaction of RANKL and RANK in testis and neutralizes at least one activity of RANKL. The antibodies or antigen binding domains, fragments or derivatives thereof may be used in the treatment, prevention or alleviation of male infertility or reduced male fertility such as oligospermia or azospermia.

Figure 1:
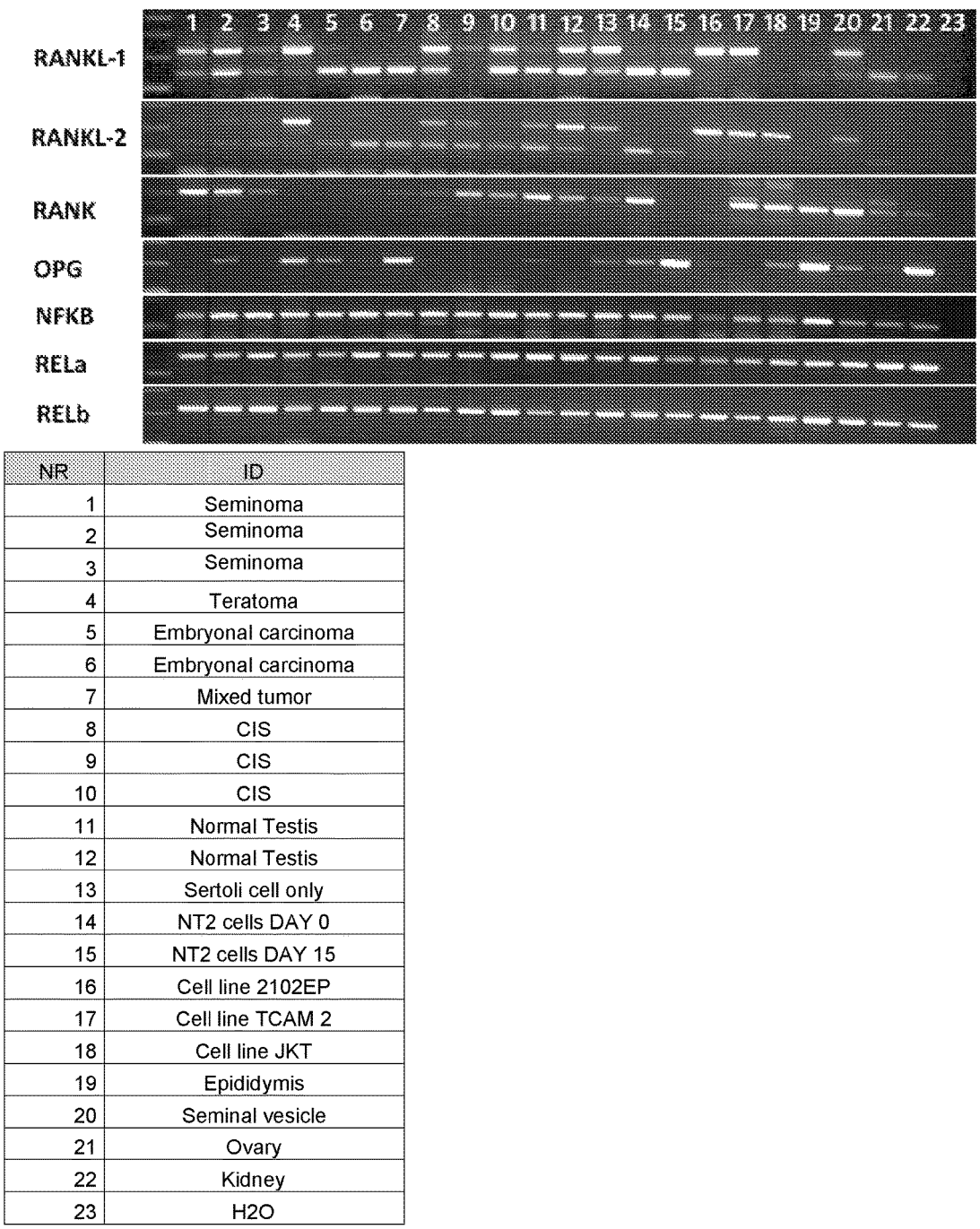
FIG. 1 shows RT-PCR of selected transcripts from human specimens marked from 1-23. Two different primersets detected two different isoforms of RANKL in normal and pathological testicular specimens. RANK and OPG are also expressed in normal and pathological testicular specimens, and OPG expression vanishes in CIS and seminoma compared with normal testis. Interestingly, only one RANKL isoform is expressed in Sertoli cell only and this isoform is not expressed in the ovary indicating a sex-specific RANKL-isoform. This isoform is not expressed in NTera2 cells, while it is expressed in TCAM2 cells. RANK is absent or weakly expressed in non-seminomas while NFKB and RELa+b are expressed in all specimens.

The present invention will now be described in more detail in the following.

DETAILED DESCRIPTION OF THE INVENTION

Definitions

Prior to discussing the present invention in further details, the following terms and conventions will first be defined:

The antibodies and antigen binding domains of the invention bind selectively to RANKL/OPGbp that is they bind preferentially to RANKL/OPGbp with a greater binding affinity than to other antigens. The antibodies may bind selectively to human RANKL/OPGbp, but also bind detectably to non-human RANKL, such as murine RANKL. Alternatively, the antibodies may bind exclusively to human RANKL or RANK, with no detectable binding to non-human RANKL or RANK, respectively.

The term "monoclonal antibody" refers to an antibody obtained from a population of substantially homogeneous antibodies, wherein each monoclonal antibody will typically recognize a single epitope on the antigen. The term "monoclonal" is not limited to any particular method for making the antibody. For example, monoclonal antibodies of the invention may be made by the hybridoma method as described in Kohler et al. Nature 256, 495 (1975) or may be isolated from phage libraries using the techniques as described herein, for example.

The term "antigen binding domain" or "antigen binding region" or "fragment or derivative thereof" refers to that portion of the selective binding agent (such as an antibody molecule) which contains the amino acid residues that interact with an antigen and confer on the binding agent its specificity and affinity for the antigen. Preferably, the antigen binding region will be of human origin. In other embodiments, the antigen-binding region can be derived from other animal species, in particular domestic animal and rodents such as rabbit, rat or hamster.

The terms "effective amount" and "therapeutically effective amount" when used in relation to an antibody or antigen binding domain, fragment or derivative thereof, immunoreactive with a RANKL peptide, refer to an amount of a selective binding agent that is useful or necessary to support an observable change in the level of one or more biological activities of RANKL, wherein said change may be either an increase or decrease in the level of RANKL activity.

In the context of the present invention, the term "sequence identity" indicates a quantitative measure of the degree of homology between two amino acid sequences or between two nucleic acid sequences. If the two sequences to be compared are not of equal length, they must be aligned to give the best possible fit, allowing the insertion of gaps or, alternatively, truncation at the ends of the polypeptide sequences or nucleotide sequences. The sequence identity can be calculated as $$\frac{(N_{ref} - N_{dif})100}{N_{ref}},$$

wherein Ndif is the total number of non-identical residues in the two sequences when aligned and wherein Nref is the number of residues in one of the sequences. Hence, the DNA sequence AGTCAGTC will have a sequence identity of 75% with the sequence AATCAATC (Ndif=2 and Nref=8). A gap is counted as non-identity of the specific residue(s), i.e. the DNA sequence AGTGTC will have a sequence identity of 75% with the DNA sequence AGTCAGTC (Ndif=2 and Nref=8).

With respect to all embodiments of the invention relating to amino acid sequences or nucleotide sequences, the percentage of sequence identity between one or 25 more sequences may also be based on alignments using the clustalW software with default settings. For nucleotide sequence alignments these settings are: Alignment=3Dfull, Gap Open 10.00, Gap Ext. 0.20, Gap separation Dist. 4, DNA weight matrix:identity (IUB). For amino acid sequence alignments the settings are as follows: Alignment=3Dfull, Gap 30 Open 10.00, Gap Ext. 0.20, Gap separation Dist. 4, Protein weight matrix: Gonnet.

Alternatively, nucleotide sequences may be analysed using programme DNASIS Max and the comparison of the sequences may be done using a service based on the two comparison algorithms called Smith-Waterman (SW) and ParAlign. The first algorithm was published by Smith and Waterman (1981) and is a well-established method that finds the optimal local alignment of two sequences. The other algorithm, ParAlign, is a heuristic method for sequence alignment; details on the method are published in Rognes (2001). Default settings for score matrix and Gap penalties as well as E-values were used.

Compound for Medical Use

In a first aspect the present invention provides a compound, which is an antagonist or inhibitor of osteoprotegerin binding protein (OPGbp)/receptor activator of NF-κB ligand (RANKL) binding to receptor activator of NF-κB (RANK), for use in stimulation of (germ) cell proliferation in the testes, and/or for use in the treatment and/or prevention of male infertility in mammals, and/or for use in inducing or improving male fertility in mammals.

The compound may in particular be an agent, which is capable of binding to RANKL Further, the compound may be a proteinaceous binding agent, which is selective for binding to RANKL.

Hence, according to particular embodiments of the present invention, the compound for use as described above is selected from the group consisting of OPG, fusion protein comprising OPG, such as Fc-OPG and human Immunoglobulin G1. In Example 4+FIG. 6 data are provided showing the effect of OPG on germ cell proliferation. In Example 5+FIGS. 8-11 data is provided showing the effect of OPG on testis parameters in mice in vivo experiments.

In a specific aspect of the invention, the invention relates to the OPG, fusion protein comprising OPG, such as Fc-OPG and human Immunoglobulin G1 for use in stimulation of (germ) cell proliferation in the testes, and/or for use in treatment and/or prevention of male infertility in mammals, and/or for use in inducing or improving male fertility in mammals, such as oligospermia or azospermia.

The nucleotide sequences and predicted amino acid sequences of murine and human RANKL are shown in SED ID NO: 1 and 3, respectively. The murine and human RANKL amino acid sequences are furthermore shown in SEQ ID NO 2 and 4, respectively.

Computer analysis of the RANKL sequence has indicated that RANKL is a Type 2 transmembrane protein. Thus, the murine RANKL protein contains, as predicted, an intracellular domain of 47 amino acids, a transmembrane domain of 21 amino acids, and an extracellular domain of 247 amino acids. The human RANKL contains, as predicted, an intracellular domain of 47 amino acids, a transmembrane domain of 21 amino acids, and an extracellular domain of 249 amino acids.

Soluble RANKL comprises a signal peptide and the extracellular domain or a fragment thereof.

RANKL is similar to other members of the TNF family having a region of amino acids between the transmembrane domain and the receptor binding domain, which does not seem to be required for biological activity. Based on alignment of the amino acid sequence, it is contemplated that the receptor binding domain of human RANKL is from about amino acid 162 to about amino acid 317 of SEQ ID NO: 4 starting with a highly conserved Ala residue amongst many family members, i.e. amino acid 162 of SEQ ID NO: 4. The murine receptor binding domain is from about amino acid 139 to about amino acid 294 of SEQ ID NO: 2.

However, the person skilled in the art would recognise that the actual receptor binding domain may be different from that predicted by alignment and computer analysis.

The N-terminal amino acid of a soluble RANKL polypeptide is expected to be within about five amino acids of the conserved Ala residue on either side. Alternatively, all or a part of the spacer region may be included in the N-terminus of the soluble RANKL peptide, as may the all or part of the transmembrane and/or intracellular domains, provided that the resulting soluble RANKL is not membrane-associated.

Thus, a soluble RANKL polypeptide will have an N-terminal amino acid selected from the group consisting of amino acids 1 through 162 of SEQ ID NO: 4 corresponding to amino acids 1 to 139 of SEQ ID NO: 2. Alternatively, the N-terminal amino acid is between 69 and 162 of SEQ ID NO: 4 (human RANKL) corresponding to amino acids 48 to 139 of SEQ ID NO: 2 (murine RANKL). Likewise, the C-terminal amino acid can be between amino acid 313 and 317 of SEQ ID NO: 4.

Since the discovery of the OPG-RANK-RANKL signalling pathway several inhibitors of RANKL function and signalling have been evaluated and/or developed as candidates for clinical use. A review of the development of RANKL inhibitors is provided in Lacey et al., Nature Reviews, (2012), Vol. 11, 401-419. These inhibitors include recombinant, full length OPG and RANK-Fc, which is a fusion protein comprising the four extracellular CRDs of RANK and the Fc-portion of human IgG.

Antibodies or Fragments Thereof Capable of Binding RANKL

According to other embodiments of the present invention, the compound for use as disclosed above is a compound which is immunoreactive with an OPGbp/RANKL peptide, in particular a human OPGbp/RANKL peptide. Alternatively, the antibody may be immunoreactive with a RANK peptide, in particular a human RANK peptide. The immunoreactive compound may in particular be selected from the group consisting of an antibody, an antigen binding domain, a fragment of an antibody, an antigen binding domain or derivative of an antibody or an antigen binding domain.

The compound, which is immunoreactive with an OPGbp/RANKL peptide, such as said antigen binding domain, said fragment of an antibody, said antigen binding domain or said derivative of an antibody or an antigen binding domain of the invention may be an antagonist compound, which decreases the level of at least one biological activity of RANKL. Antagonist antibodies of RANKL may also be referred to as inhibitory or neutralizing antibodies of RANKL.

Likewise, the compound, which is immunoreactive with RANK peptide, such as said antigen binding domain, said fragment of an antibody, said antigen binding domain or said derivative of an antibody or an antigen binding domain of the invention may be an antagonist compound, which decreases the level of at least one biological activity of RANK. Antagonist antibodies of RANK may also be referred to as inhibitory or neutralizing antibodies of RANK.

In particular, the compound for use according to the invention may be an inhibitor of RANKL signaling. In the context of the present invention, the compound including the said antigen binding domain, said fragment of an antibody, said antigen binding domain or said derivative of an antibody or an antigen binding domain, may be capable of substantially inhibits binding of a ligand to a receptor, such as binding of RANKL to RANK.

An antibody substantially inhibits binding of a ligand to a receptor when an excess of antibody reduces the quantity of receptor bound to counter-receptor or ligand by at least about 20%, 40%, 60%, 80%, 85%, 90% or more (as measured in an in vitro competitive binding assay).

The compound for use according to the present invention, may be a compound selected from the group consisting of a polyclonal antibody, a monoclonal antibody, an antibody wherein the heavy chain and the light chain are connected by a flexible linker, an Fv molecule, an antigen binding fragment, a Fab fragment, a Fab' fragment, a F(ab')2 molecule, a fully human antibody, a humanized antibody, and a chimeric antibody.

The terms "heavy chain" and "light chain" of said antibody each includes any polypeptide having sufficient variable region sequence to confer specificity for an OPGbp/RANKL peptide. A full-length heavy chain includes a variable region domain, VH, and three constant region domains, CH1, CH2, and CH3. The VH domain is at the amino-terminus of the polypeptide, and the CH3 domain is at the carboxy-terminus. The term "heavy chain", as used herein, encompasses a full-length heavy chain and fragments thereof. A full-length light chain includes a variable region domain, VL, and a constant region domain, CL. Like the heavy chain, the variable region domain of the light chain is at the amino-terminus of the polypeptide. The term "light chain", as used herein, encompasses a full length light chain and fragments thereof. A Fab fragment is comprised of one light chain and the CH1 and variable regions of one heavy chain. The heavy chain of a Fab molecule cannot form a disulfide bond with another heavy chain molecule. A Fab' fragment contains one light chain and one heavy chain that contains more of the constant region, between the CH1 and CH2 domains, such that an interchain disulfide bond can be formed between two heavy chains to form a F (ab') 2 molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain which forms an antigen-binding region. Single chain antibodies are discussed in detail in WO 88/01649 and U.S. Pat. Nos. 4,946,778 and 5,260,203.

As described above, anti-RANKL/OPGbp antibodies and antigen binding domains, which inhibit at least one activity of OPBbp/RANKL have been identified. Embodiments of the invention include antibodies comprising a heavy chain Fab and further comprising a kappa or lambda light chain sequence. The antibodies of the invention further comprise a human Fc region from any isotype, either IgG, IgM, IgA, IgE, or IgD. Preferably, the Fc region is from human IgG, such as IgG1, IgG2, IgG3, or IgG4.

The invention also provides for antibodies or antigen binding domains which comprise fragments, variants, or derivatives of the Fab sequences disclosed herein. Fragments may include variable domains of the light or heavy chain Fab sequences, which are typically joined to light or heavy constant domains. The antibodies may be typically associated with constant regions of the heavy and light chains to form full-length antibodies.

Antibodies and antigen binding domains, and fragments, variants and derivatives thereof, of the invention will retain the ability to bind selectively to an RANKL polypeptide, preferably to a human RANKL polypeptide. In one embodiment, the antibody and antigen binding domains, and fragments, variants and derivatives thereof, will bind an RANKL polypeptide with a dissociation constant (KD) of about ≤1 nM, or alternatively ≤0.1 nM, or alternatively ≤10 pM or alternatively ≤10 pM.

Antibodies of the invention include polyclonal, monospecific polyclonal, monoclonal, recombinant, chimeric, humanized, fully human, single chain and/or bispecific antibodies. Antibody fragments include those portions of an anti-RANKL antibody, which bind to an epitope on an RANKL polypeptide. Examples of such fragments include Fab F(ab'), F(ab)', Fv, and sFv fragments. The antibodies may be generated by enzymatic cleavage of full-length antibodies or by recombinant DNA techniques, such as expression of recombinant plasmids containing nucleic acid sequences encoding antibody variable regions.

Polyclonal antibodies are heterogeneous populations of antibody molecules derived from the sera of animals immunized with an antigen. An antigen is a molecule or a portion of a molecule capable of being bound by an antibody, which is additionally capable of inducing an animal to produce antibody capable of binding to an epitope of that antigen. An antigen can have one or more epitopes. The specific reaction referred to above is meant to indicate that the antigen will react, in a highly selective manner, with its corresponding antibody and not with the multitude of other antibodies, which can be evoked by other antigens.

Polyclonal antibodies directed toward a RANKL polypeptide generally are raised in animals (e.g., rabbits or mice) by multiple subcutaneous or intraperitoneal injections of RANKL and an adjuvant. In accordance with the invention, it may be useful to conjugate an RANKL polypeptide, or a variant, fragment, or derivative thereof to a carrier protein that is immunogenic in the species to be immunized, such as keyhole limpet heocyanin, serum, albumin, bovine thyroglobulin, or soybean trypsin inhibitor. Also aggregating agents such as alum are used to enhance the immune response. After immunization, the animals are bled and the serum is assayed for anti-RANKL antibody titer.

Monoclonal antibodies (mAbs) contain a substantially homogeneous population of antibodies specific to antigens, which population contains substantially similar epitope binding sites. Such antibodies may be of any immunoglobulin class including IgG, IgM, IgE, IgA, IgD and any subclass thereof. A hybridoma producing a monoclonal antibody of the present invention may be cultivated in vitro, in situ, or in vivo. Production of high titers in vivo or in situ is a preferred method of production.

Monoclonal antibodies directed toward OPGbp/RANKL are produced using any method, which provides for the production of antibody molecules by continuous cell lines in culture. Examples of suitable methods for preparing monoclonal antibodies include hybridoma methods of Kohler et al., Nature 256, 495-497 (1975), and the human B-cell hybridoma method, Kozbor, J. Immunol. 133, 3001 (1984); Brodeur et al., Monoclonal Antibody Production Techniques and Applications, pp. 51-63 (Marcel Dekker, Inc., New York, 1987); and Harlow and Lane, Antibodies: A Laboratory Manual, Cold Spring Harbor Laboratory (1988); the contents of which references are incorporated entirely herein by reference.

A particularly preferred method for producing monoclonal antibodies directed towards OPGbp/RANKL involves immunizing the XenoMouse as described in Green, LL, J. Immunol. Methods (1999), Vol. 231, 11-25, with a OPGbp/RANKL peptide, such as a full-length human RANKL protein.

Preferred anti-RANKL or anti-RANK antibodies include monoclonal antibodies, which will inhibit partially or completely the binding of human RANKL to its cognate receptor, RANK, or an antibody having substantially the same specific binding characteristics, as well as fragments and regions thereof. Preferred methods for determining monoclonal antibody specificity and affinity by competitive inhibition can be found in Harlow et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc and Wiley Interscience, N.Y., (1992, 1993), and Muller, Meth. Enzymol., 92:589-601 (1983).

Chimeric antibodies are molecules in which different portions are derived from different animal species, such as those having a variable region derived from a murine monoclonal antibody and a human immunoglobulin constant region. Chimeric antibodies are primarily used to reduce immunogenicity in application and to increase yields in production, for example, where murine monoclonal antibodies have higher yields from hybridomas but higher immunogenicity in humans, such that human/murine chimeric monoclonal antibodies are used. Chimeric antibodies and methods for their production are known in the art. See Cabilly et al., Proc. Natl. Acad. Sci. USA, 81:3273-3277 (1984); Morrison et al., Proc. Natl. Acad. Sci. USA, 81:6851-6855 (1984); Boulianne et al., Nature, 312:643-646 (1984); Neuberger et al., Nature, 314:268-270 (1985); Liu et al., Proc. Natl. Acad. Sci. USA, 84:3439-3443 (1987); and Harlow and Lane Antibodies: A Laboratory Manual, Cold Spring Harbor Laboratory (1988).

For example, chimeric monoclonal antibodies of the invention may be used as a therapeutic. In such a chimeric antibody, a portion of the heavy and/or light chain is identical with or homologous to corresponding sequences in antibodies derived from a particular species or belonging to one particular antibody class or subclass, while the remainder of the chain(s) is identical with or homologous to corresponding sequence in antibodies derived from another species or belonging to another antibody class or subclass, as well as fragments of such antibodies, so long as they exhibit the desired biological activity (see U.S. Pat. No. 4, 816, 567 ; Morrison et al., Proc. Natl. Acad. Sci. , 81, 6851-6855 (1985).

The term "chimeric antibody", as used herein, includes monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer (H2L2) formed by two HL dimers associated through at least one disulfide bridge. A polyvalent chimeric antibody can also be produced, for example, by employing a CH region that aggregates (e.g., from an IgM H chain, or [micro] chain).

Murine and chimeric antibodies, fragments and regions of the present invention may comprise individual heavy (H) and/or light (L) immunoglobulin chains. A chimeric H chain comprises an antigen binding region derived from the H chain of a non-human antibody specific for RANKL, which is linked to at least a portion of a human H chain C region (CR), such as CH1 or CH2.

A chimeric L chain according to the present invention comprises an antigen binding region derived from the L chain of a non-human antibody specific for RANKL, linked to at least a portion of a human L chain C region (CL).

Selective binding agents, such as antibodies, fragments, or derivatives, having 15 chimeric H chains and L chains of the same or different variable region binding specificity, can also be prepared by appropriate association of the individual polypeptide chains, according to known method steps, e.g., according to Ausubel et al., eds. Current Protocols in Molecular Biology, Wiley Interscience, N.Y. (1993), and Harlow et al., Antibodies: A Laboratory Manual, Cold Spring Harbor Laboratory Press, Cold Spring Harbor, N.Y. (1988). The contents of these references are incorporated entirely herein by reference. With this approach, hosts expressing chimeric H chains (or their derivatives) are separately cultured from hosts expressing chimeric L chains (or their derivatives), and the immunoglobulin chains are separately recovered and then associated. Alternatively, the hosts can be co-cultured and the chains allowed to associate spontaneously in the culture medium, followed by recovery of the assembled immunoglobulin, fragment or derivative.

As an example, the antigen-binding region of the selective binding agent (such as a chimeric antibody) of the present invention is preferably derived from a non-human antibody specific for human RANKL. Preferred sources for the DNA encoding such a non-human antibody include cell lines, which produce antibodies, such as hybrid cell lines commonly known as hybridomas.

The invention also provides for fragments; variants and derivatives, and fusions of anti-RANKL antibodies, wherein the terms "fragments", "variants", "derivatives" and "fusions" are defined above. The invention provides for fragments, variants, derivatives, and fusions of anti-RANKL antibodies, which are functionally similar to the unmodified anti-RANKL antibody, that is, they retain at least one of the activities of the unmodified antibody. In addition to the modifications set forth above, also included is the addition of genetic sequences coding for cytotoxic proteins such as plant and bacterial toxins. The fragments, variants, derivatives and fusions of anti-RANKL antibodies can be produced from any of the hosts of this invention.

Suitable fragments include, for example, Fab, Fab', F(ab')2 Fv and scFv. These fragments lack the Fc fragment of an intact antibody, clear more rapidly from the circulation, and can have less non-specific tissue binding than an intact antibody. See Wahl et al., J. Nucl. Med., 24:316-325 (1983). These fragments are produced from intact antibodies using methods well known in the art, for example by proteolytic cleavage with enzymes such as papain (to produce Fab fragments) or pepsin (to produce F(ab')2 fragments). The identification of these antigen binding regions and/or epitopes recognized by monoclonal antibodies of the present invention provides the information necessary to generate additional monoclonal antibodies with similar binding characteristics and therapeutic or diagnostic utility that parallel the embodiments of this application.

In particular embodiments, the antibody or antigen binding domain, fragment or derivative thereof according to the invention is immunoreactive with a peptide or polypeptide comprising or consisting of an amino acid sequence selected from the group consisting of:
  i) the amino acid sequence set forth in SEQ ID NO: 2 or SEQ ID NO: 4;
  ii) the amino acid sequence encoded by a DNA molecule comprising a nucleotide sequence as shown in nucleotides 1 to 951 of SEQ ID NO: 3;
  iii) the amino acid sequence set forth in SEQ ID NO: 11;
  iv) a subsequence of any one of the sequences set forth in i)-iii) said subsequence being able to bind to a RANK polypeptide as set forth in SEQ ID NO: 11; and
  iv) a sequence having at least 90% sequence identity to any of the sequences set forth in i)-iii); such as at least 91, 92, 93, 94, 95, 96, 97, 98, 99 or 99.5% sequence identity to any of the sequences set forth in i)-iii)

In a specific embodiment, the amino terminal amino acid residue in the above-mentioned subsequence is any one of amino acid residues no. 1-162 in SEQ ID NO. 4.

According to a further embodiment, the carboxy terminal amino acid residue in said subsequence is any one of amino acid residues no. 313-317 in SEQ ID NO: 4.

The subsequence may, in addition, be the amino acid sequence encoded by a DNA comprising a nucleotide sequence as shown in nucleotides 484 to 951 of SEQ ID NO: 3.

The invention provides for anti-RANKL/OPGbp antibodies, or antigen binding domains, which recognize and bind to inhibiting and/or neutralizing epitopes on RANKL/OPGbp. As a result of this binding, an anti-RANKL antibody may partially or completely inhibit binding of RANKL to its receptor, or may in turn partially or completely increase spermatogenesis. More particularly, the invention provides for anti-RANKL antibodies, which recognize and bind to an epitope comprising a portion of the amino acid sequence of a DE domain of RANKL/OPGbp (a "DE epitope"). A DE region of RANKL spans approximately the D and E beta sheet regions and intervening loop sequence (a "DE loop"). The DE domain in human RANKL comprises from about amino acid residue 212 to about amino acid residue 250 inclusive. The human RANKL/OPGbp DE domain is shown in SEQ ID NO: 5. However, the amino acid sequence and endpoints of the DE domain of human RANKL are merely exemplary, and it is understood that DE domains may have sequences and endpoints, which vary from those in human RANKL. The invention encompasses antibodies, which bind to such variable DE domains.

While it is contemplated that an anti-RANKL/OPGbp antibody, or an antigen-binding domain, may bind at any location within a DE domain, a preferred embodiment is an anti-RANKL/OPGbp antibody, which binds to at least part of a DE loop. The DE loop in human RANKL spans approximately five amino acids and is located at about residues 230-234 inclusive. The DE loop in human RANKL/OPGbp has the sequence DLATE. However, the amino acid sequence and endpoints of the DE loop of human RANKL/OPGbp are merely exemplary and it is understood that DE loops could have sequences and endpoints, which vary from those in human RANKL/OPGbp. The invention concerns antibodies, which bind to such variable DE loops.

While the antibodies of the invention are characterized in part by the amino acid sequences on RANKL/OPGbp to which they bind, it is understood by one skilled in the art that a DE epitope on RANKL/OPGbp recognized by an antibody typically comprises a three dimensional structure which may involve amino acids outside the DE domain. In a linear representation of an RANKL/OPGbp sequence, amino acids comprising the DE epitope may be distant from the DE domain, but in a three-dimensional structure of RANKL/OPGbp, amino acids of the DE epitope will likely be in proximity to the DE domain. Thus, it is understood that binding of an anti-RANKL/OPGbp antibody to a DE epitope may involve amino acids other than those in the DE region. Nonetheless, it has been shown that amino acid residues in the DE loop, especially some or all of the residues in the sequence DLATE, are involved in antibody binding to RANKL/OPGbp and inhibition of RANKL/OPGbp activity.

Variants of selective binding agents are also provided. In one embodiment, variants of antibodies and antigen binding domains comprise changes in light and/or heavy chain amino acid sequences that are naturally occurring or are introduced by in vitro engineering of native sequences using recombinant DNA techniques. Naturally occurring variants include "somatic" variants which are generated in vivo in the corresponding germ line nucleotide sequences during the generation of an antibody response to a foreign antigen.

Variants of anti-RANKL/OPGbp antibodies and antigen binding domains are also prepared by mutagenesis techniques known in the art. In one example, amino acid changes may be introduced at random throughout an antibody-coding region and the resulting variants may be screened for a desired activity, such as binding affinity for RANKL/OPGbp. Alternatively, amino acid changes may be introduced in selected regions of an anti-RANKL/OPGbp antibody, such as in the light and/or heavy chain CDRs, and framework regions, and the resulting antibodies may be screened for binding to RANKL or some other activity. Amino acid changes encompass one or more amino acid substitutions in a CDR, ranging from a single amino acid difference to the introduction of all possible permutations of amino acids within a given CDR, such as CDR3. In another method, the contribution of each residue within a CDR to RANKL/OPGbp binding may be assessed by substituting at least one residue within the CDR with alanine (Lewis et al., Mol. Immunol. 32. 1065-1072 (1995)). Residues that are not optimal for binding to RANKL may then be changed in order to determine a more optimal sequence. Also encompassed are variants generated by insertion of amino acids to increase the size of a CDR, such as CDR3. For example, most light chain CDR3 sequences are nine amino acids in length. Light chain CDR3 sequences in an antibody which are shorter than nine residues may be optimized for binding to RANKL/OPGbp by insertion of appropriate amino acids to increase the length of the CDR.

In one embodiment, antibody or antigen binding domain variants comprise one or more amino acid changes in one or more of the heavy or light chain CDR1, CDR2 or CDR3 and optionally one or more of the heavy or light chain framework regions FR1, FR2 or FR3. Amino acid changes comprise substitutions, deletions and/or insertions of amino acid residues. The aforementioned "AT" heavy and light chain variable region variants may further comprise one or more amino acid changes in the framework regions. In one example, one or more amino acid changes may be introduced to substitute a somatically mutated framework residue with the germline residue at that position. When the aforementioned amino acid changes are substitutions, the changes may be conservative or non-conservative substitutions.

In a particular embodiment, the antibody or antigen binding domain of the invention is immunoreactive with an amino acid sequence selected from the group consisting of:
  i) the amino acid sequence set forth in SEQ ID NO: 5 (Human RANKL D-E domain: GFYYLYANICFRH-HETSGDLATEYLQLMVYVTKTSIKIP); and
  ii) a subsequence of the amino acid in i), said subsequence or variant comprising the sequence set forth in SEQ ID NO.: 6 (Human DE epitope DLATE).

In another embodiment, the antibody or antigen-binding domain according to the invention is a human monoclonal antibody or antigen binding domain. The antibody may also be a full length human monoclonal IgG2.

Generally, antibodies of the IgG2 isotype are preferable because antibodies of this isotype have little associated effector function, such as antibody-dependent cell-mediated cytotoxicity.

In a specific embodiment, the antibody according to the invention has a heavy chain comprising an amino acid selected from the group consisting of:
  i) the amino acid set forth in SEQ ID NO: 7 (heavy chain of αRANKL-1);
  ii) a subsequence of the amino sequence set forth in SEQ ID NO: 7; and
  iii) an amino acid sequence having at least 90% sequence identity to any of the amino acid sequences set forth in i) and ii), such as at least 91, 92, 93, 94, 95, 96, 97, 98, 99 or 99.5% sequence identity to any of the sequences set forth in i) and ii).

According to another embodiment, the subsequence of the amino acid sequence set forth in SEQ ID NO: 7 comprises the sequence set forth in SEQ ID NO: 8 (variable region of heavy chain).

In a further particular embodiment, the antibody according to the invention has a light chain comprising an amino acid sequence selected from the group consisting of:
  i) the amino acid set forth in SEQ ID NO: 9(light chain of αRANKL-1);
  ii) a subsequence of the amino sequence set forth in i); and
  iii) an amino acid sequence having at least 90% sequence identity to any of the amino acid sequences set forth in i) and ii) such as at least 91, 92, 93, 94, 95, 96, 97, 98, 99 or 99.5% sequence identity to any of the sequences set forth in i) and ii).

The above mentioned subsequence of the amino acid sequence set forth in SEQ ID NO: 9 comprises the sequence set forth in SEQ ID NO: 10 (variable region of light chain).

In a preferred embodiment, the antibody for use according to the invention is denosumab. In Example 4+FIGS. 6 and 7, data are provided showing the effect of denosumab on germ cell proliferation. These results are in accordance with the results shown for OPG.

Thus, a specific aspect of the invention relates to denosumab for use in stimulation of (germ) cell proliferation in the testes, and/or for use in treatment and/or prevention of male infertility in mammals, and/or for use in inducing or improving male fertility in mammals, such as oligospermia or azospermia.

Denosumab is the common name for fully human monoclonal antibody against RANKL having a molar mass of 144.7 kDa (also known under the synonym AMG162). Denosumab is marketed under the tradenames Prolia, Xgeva, and Ranmark XGEVA. Denosumab can further more be identified by the following identifiers: the CAS Registry Number of denosumab is 615258-40-7, the Anatomical Therapeutic Chemical (ATC) Classification System code is M05BX04, the ChEMBL compound ID is CHEMBL1237023, the UNique Ingredient Identifier (UNII) is 4EQZ6YO2HI, the KEGG kode (Kyoto Encyclopedia of Genes and Genomes) is D03684.

The compounds according the present invention is used in the prevention and/or treatment of oligospermia of the prevention and/or treatment of azoospermia.

Moreover, the compounds according to the present invention may be administered intravenously or subcutaneously. In particularly, the compounds may be administered subcutaneously, intra-testicularly or in the genital region once every 2 to 8 weeks, preferably every 4 weeks at a dose of 20-120 mg, preferably 60-120 mg. The compound according to the present invention may also be administered in the scrotal region.

In particular, the male subject may be a subject in whom there is spermatogenic failure in and/or reduced OPG expression in peritubular cells a tissue biopsy taken from the testes.

Thus, in a specific embodiment, the compound according to the present invention may be administered to a male subject who does not suffer from testicular cancer at any stage, which is detectable by histological analysis of a tissue sample of the testis from said subject, such as a human male subject at the age of 15-55 years.

The present invention also relates to compositions comprising the compounds according to the present invention for use in the treatment and/or prevention of male infertility in mammals, and/or for improving male fertility in mammals.

The composition of the present invention may be a pharmaceutical composition, which comprises one or more physiologically acceptable carriers, excipients and/or diluents. The composition may, in addition, one or more stabilizing agents and/or one or more buffering agents.

Moreover, compositions of the present invention may comprise at least one stabilizing agent, such as a surfactant, in particular a surfactant selected from polysorbate and polyoxypropylene-polyethylene esters (Pluronic®). The surfactant may also be selected from polysorbate 20 and polysorbate 80.

The surfactant may be present at a concentration of 0.001-1%, such as 0.002-0.5%, such as 0.004%, or 0.01%

The composition according to the present invention may furthermore comprise sorbitol, acetate, sodium hydroxide and water for injection. The pH of said composition is, preferably, between 5.2 and 6.5, such as between 5.5 and 6.5, such as between 4.5 and 5.5, such as 6.3 or such as 5.2

Finally, the composition may, in addition, comprise one or more components selected from: Calcium and Vitamin D.

The present invention also provides for methods of treating and/or preventing male infertility in a mammal, and/or for improving male fertility in a mammal, said method comprising administering a therapeutically effective amount of a compound or composition according to the present invention.

The mammal may be a male (human) subject who does not suffer from testicular cancer at any stage, which is detectable by histological analysis of a tissue sample of the testis from said subject, such as a human male subject at the age of 15-55 years.

In an embodiment, the mammal is selected from the group consisting of human, pig, monkey, cow, sheep, mice, and horse.

The method according to the present invention comprises administration intravenously or subcutaneously of the compounds or compositions of the present invention. In particularly, the compounds or compositions of the present invention may by administered subcutaneously, intra-intesticularly or in the genital region once every 2 to 12 weeks, preferably every 4 weeks at a dose of 20-120 mg, preferably 60-120 mg. The compound or compositions according to the present invention may also be administered in the scrotal region.

It should be noted that embodiments and features described in the context of one of the aspects or embodiments of the present invention may also apply to the other aspects or embodiments of the invention.

All patent and non-patent references cited in the present application, are hereby incorporated by reference in their entirety.

The invention will now be described in further details in the following non-limiting examples.

EXAMPLES

Example 1

This example illustrates the preparation of monoclonal antibodies against RANKL.

Preparations of purified recombinant RANKL, for example, or transfixed cells expressing high levels of RANKL, are employed to generate monoclonal antibodies against RANKL using conventional techniques, such as those disclosed in U.S. Pat. No. 4,411,993. DNA encoding RANKL can also be used as an immunogen, for example, as reviewed by Pardoll and Beckerleg in Immunity 3:165, 1995. Such antibodies are likely to be useful in interfering with RANKL signaling (antagonistic or blocking antibodies).

To immunize rodents, RANKL immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10-100 pig subcutaneously into a selected rodent, for example, BALB/c mice or Lewis rats. DNA may be given intradermally (Raz et al., Proc. Natl. Acad. Sci. USA 91:9519, 1994) or intramuscularly (Wang et al., Proc. Natl. Acad. Sci. USA 90:4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis.

Following detection of an appropriate antibody titer, positive animals are given an intravenous injection of antigen in saline. Three to four days later, the animals are sacrificed, splenocytes harvested, and fused to a murine myeloma cell line (e.g., NS 1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with RANKL, for example, by adaptations of the techniques disclosed by Engvall et al., Immunochem. 8:871 (1971) and in U.S. Pat. No. 4,703,004. A preferred screening technique is the antibody capture technique described by Beckman et al., J. Immunol. 144:4212 (1990). Positive clones are then injected into the peritoneal cavities of syngeneic rodents to produce ascites containing high concentrations (>1 mg/ml) of anti-RANK monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to RANKL protein. Using the methods described herein to monitor the activity of the mAbs, both blocking (i.e., antibodies that bind RANKL and inhibit binding to RANK) and non-blocking (i.e., antibodies that bind RANKL and do not inhibit binding) are isolated.

Example 2

Introduction

RANKL signalling is important for bone homeostasis, immune system and lactation. RANKL is a transmembrane protein with an extracellular ligand-domain that specifically binds to RANK, a receptor situated in the membrane of the neighboring cell. Binding and activation of RANK induces intracellular signalling often through NFKB activation, which influences cell cycle. Interaction between RANKL and RANK is modulated by OPG secretion from cells in the vicinity as OPG binds to the extracellular domain of RANKL and prevents RANK activation. So the biological effect of RANKL depends on the presence and abundance of RANKL, RANK and OPG. To make things even more complicated, RANKL exists in three different isoforms 1, 2, and 3. One transmembrane form and one cytoplasmic and another secreted form. The different isoforms may not always induce the same effect and the cytoplasmic non-secreted form is in general an inhibitor of RANKL expression. This means that inhibition of RANKL potentially give opposite effects depending on the expression of the specific isoform in the model.

Downstream signalling of RANK is influenced by the presence and activity of TRAF1-6. Depending on which cofactor is present, RANK will transmit different signals and thus mediate a different response to the same external stimuli. Besides TRAFs, RANK is also influenced by REL a and b and on the presence of the key downstream signalling mechanism NFKB.

We have previously shown that the Vitamin D receptor (VDR), and all the vitamin D metabolizing enzymes are expressed in the male ejaculatory duct, germ cells and mature spermatozoa. RANKL is a classical vitamin D regulated gene as it contains Vitamin D response elements in the promoter and vitamin D induces transcription of the RANKL gene. RANKL has never previously been associated with testicular function and male fertility and has never been shown to be expressed in the gonad. Ablation of RANKL, RANK or OPG in mice does apparently not cause male infertility, but so far there has not been conducted a fertility study or any reports on semen quality.

Denosumab is man-made specific inhibitor of human RANKL signalling as it does not inhibit the murine RANKL or TRAIL signalling. In monkeys, a 10-fold higher denosumab dose than used regularly did not cause any major testicular histological abnormalities or low sperm motility, but fertility testing was not performed. During our work with VDR we found that RANKL was expressed at the RNA level and here we investigated whether RANKL, RANK and OPG are expressed in the gonad of mice and men.

Material and Methods

Human Tissue Samples

Patients were recruited from the andrology clinic at Copenhagen University Hospital (Rigshospitalet), Denmark in accordance with the Helsinki Declaration after approval from the local ethics committee. Adult testis samples were obtained from orchidectomy specimens performed due to TGCT. Tissue surrounding the tumor contained tubules with either CIS cells or normal/impaired spermatogenesis. Each sample was divided into fragments, which were either snap-frozen and stored at −80° C. for RNA extraction or fixed overnight at 4° C. in formalin or paraformaldehyde and subsequently embedded in paraffin. An experienced pathologist evaluated all samples and immunohistochemical (IHC) markers were used for TGCT to ensure the histological subtypes of the tumors.

Mouse Tissue Samples

Leuven Vdr−/− mice and controls were generated and bred using a standard rodent diet (1.0% calcium, 0.7% phosphorus, Sniff R/M-H). All animals were treated according to the National Institutes of Health Guide for the Care and Use of Laboratory Animals, and all experiments were approved by the 'Ethical Committee Animal Tests' of the KU Leuven. Representative groups of mice were killed at 10 or 15 weeks of age, respectively. Mice were exsanguinated under anaesthesia and serum was collected for hormone measurements. Each testis was divided into fragments, which were either snap-frozen and stored at −80° C. for RNA or protein extraction or fixed overnight at 4° C. in paraformaldehyde (PFA) or Bouin's solution and embedded in paraffin.

Tissue preparation, quantitative RT-PCR (qRT-PCR) and western blot RNA and cDNA preparation and subsequent qRT-PCR were performed. qRT-PCR was performed using specific primers targeting each mRNA. Representative bands from each primer combination were sequenced for verification (Eurofins MWG GmbH, Germany). Changes in gene expression were determined by comparing with RPS20 or B2m (β2-microglobulin)

Immunohistochemistry (IHC)

All tissue were stained immunohistochemically for RANKL, OPG, and RANK. Briefly, the immunohistochemical (IHC) staining was performed according to a standard indirect peroxidase method and counterstained with Meyer's haematoxylin. All experiments were performed with a negative control staining without the primary antibody. Serial sections were used to examine concomitant expression of RANKL, RANK and OPG, Antigen retrieval was accomplished by microwaving the sections for 15 min in TEG buffer (Tris 6.06 g, EGTA 0.95 g in 5 I, pH 9.0). Sections were washed in 2% hydrogenperoxid to block endogenous peroxidase. Afterwards, all sections were incubated with 2% non-immune goat serum or mouse serum (Zymed Histostain kit, San Francisco, Calif., USA) in Tris buffered saline (TBS) to minimize cross-reactivity. Primary antibodies were purchased from Santa Cruz Biotechnology Inc., Santa Cruz, Calif. All antibodies were tested by western blotting and initial experiments were carried out with different antibody dilutions (1:50 to1:500), different buffers (TEG, citrate, Urea) and with different fixatives (formalin, ethanol and none). After 16 h of incubation at 4° C., the sections were incubated with biotinylated goat anti-rabbit IgG (Zymed Histostain kit) or biotinylated donkey antigoat IgG (1:400), before a peroxidase-conjugated streptavidin complex (Zymed Histostain kit) was used as a tertiary layer. Visualization was performed with amino ethyl carbasole (Zymed Histostain kit). The slides were washed with TBS between incubation steps.

Results:

Human

Figure 3:
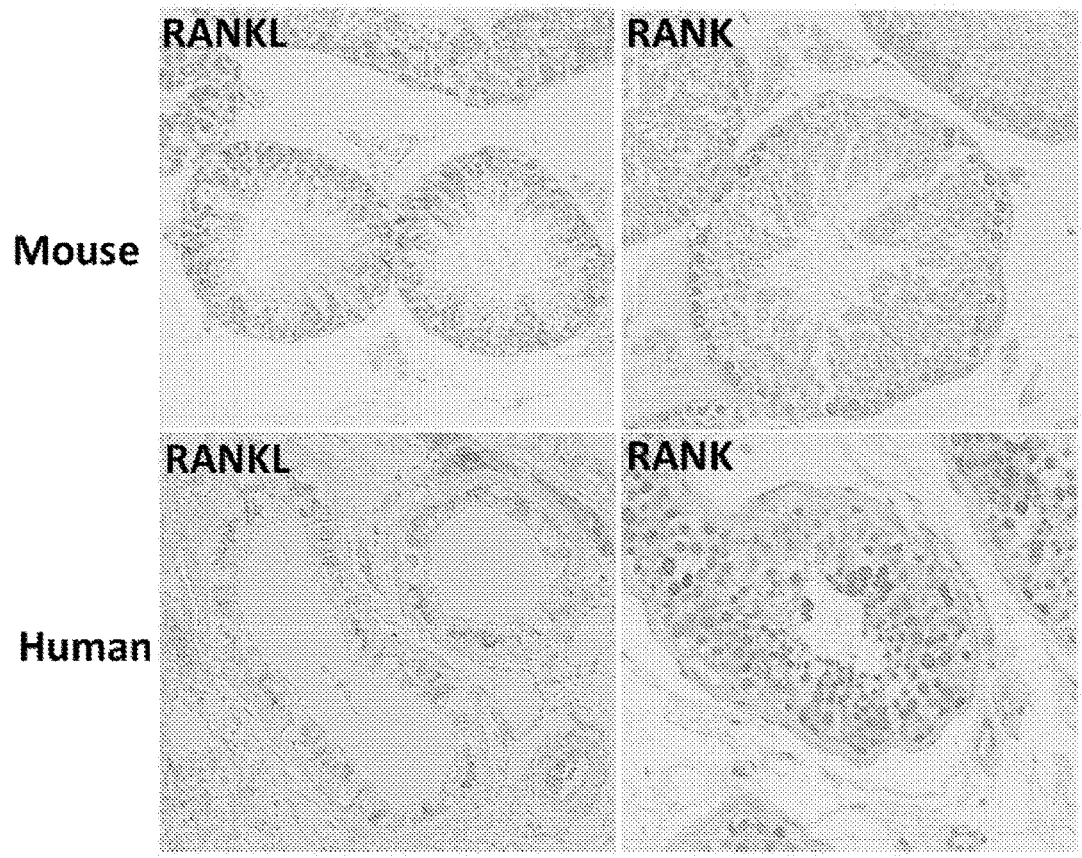
FIG. 3 shows immunohistochemical expression of RANKL and RANK in normal testis and carcinoma in situ tubules obtained from humans besides expression in normal mouse testis. RANK is expressed in germ cells, while RANKL is expressed in Sertoli and later stages of germ cells.

At the RNA level, we found a marked expression of RANKL, RANK and OPG in the testis containing normal tubules with complete spermatogenesis (FIG. 1). All the isoforms of RANKL was expressed in the testis. Only one isoform was expressed in Sertoli cell only, which differed from the isoform being expressed in the ovary. At the protein level, we found expression of RANKL in adult Sertoli cells and in the male germ cells (FIG. 3). The expression was cytoplasmic and transmembrane.

The intensity of the staining varied from very low to normal, but RANKL expression was detectable in the vast majority of Sertoli cells and in many germ cells. The presence of RANKL in Sertoli cell only tubules indicates that one isoform is Sertoli specific, while other forms also may be present in germ cells. Rank was exclusively expressed in the germ cells with a prominent expression in spermatogonia and spermatocytes. Again, the expression was mixed cytoplasmic and membranous. OPG was expressed mainly in the peritubular cells and the expression was mainly cytoplasmic. Interestingly the expression of OPG lowered in tissue containing CIS, which may expose the CIS cells to higher RANKL exposure.

Mouse

Figure 2A:
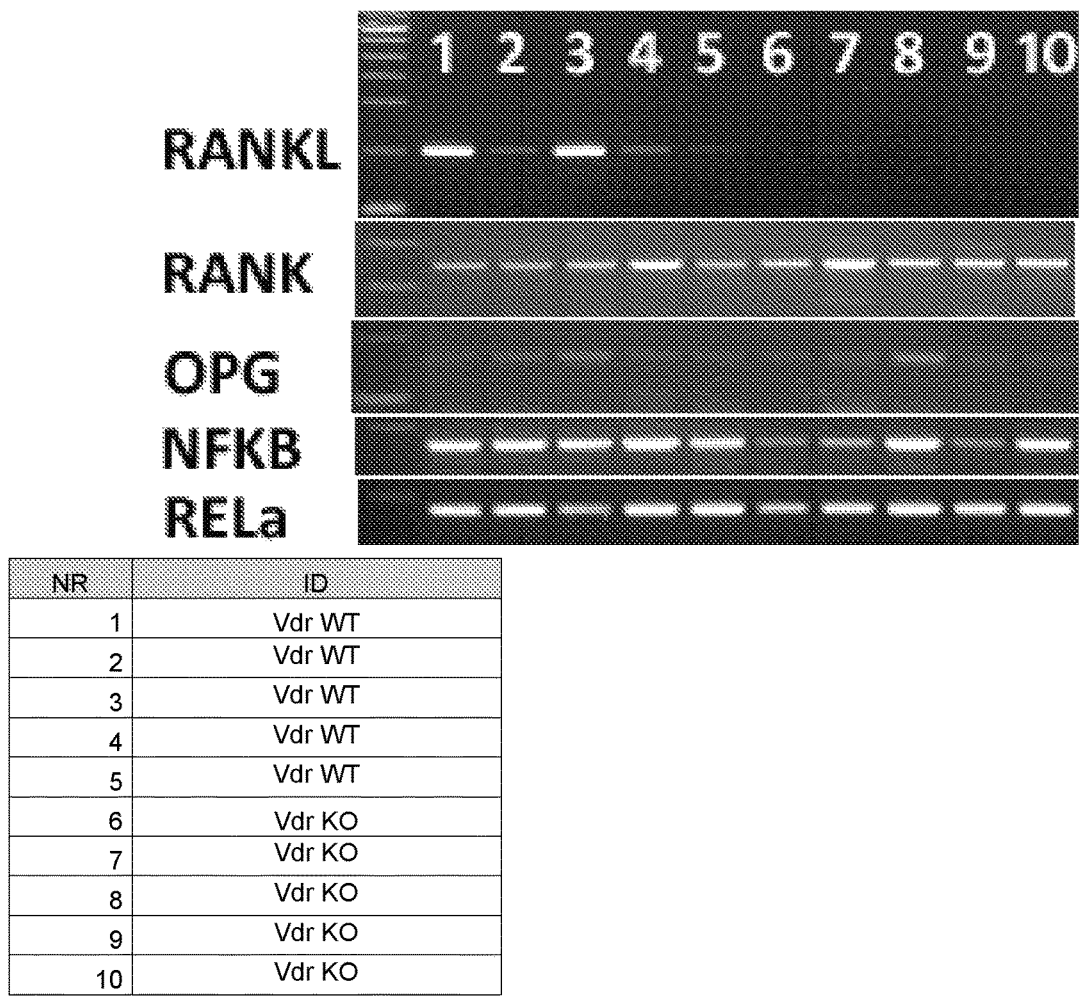
FIG. 2A shows RT-PCR of selected transcripts from Swiss mice with a normal vitamin D receptor (Vdr wt) or with a mutated and inactive vitamin D receptor (Vdr KO). A primerset detects RANKL in normal mice, while the expression is low or absent in Vdr KO mice. RANK, OPG, RELa are expressed in all animals, while NFKB appears to be lower expressed in Vdr KO mice.
Figure 2B:
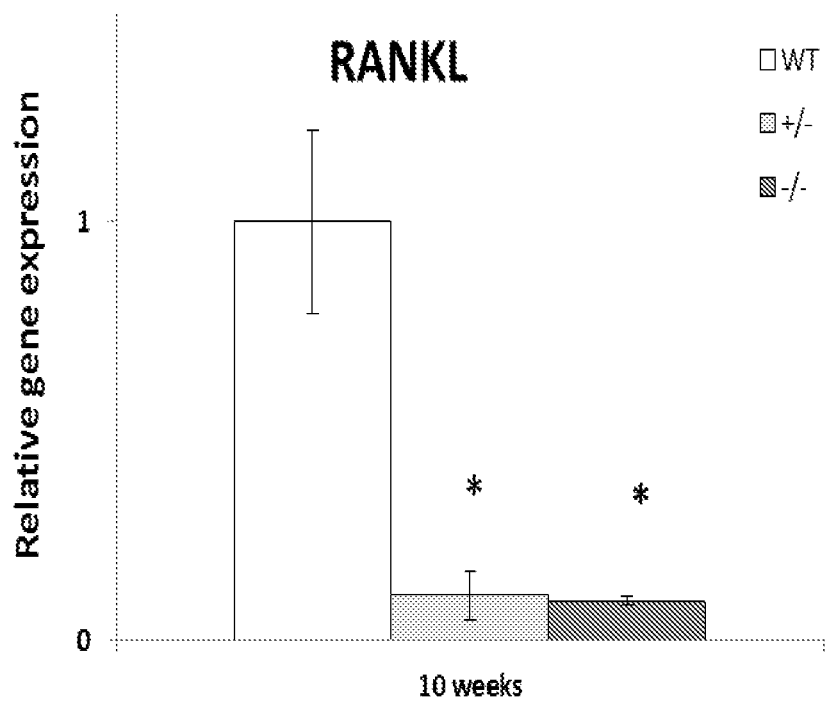
FIG. 2B shows quantitative PCR of RANKL from mice with a normal Vdr (wt), one inactive allelle (+/−) or two inactivated alleles (−/−). The significant downregulation of RANKL in both heterozygote and homozygote mutant mice indicates that the main isoform is RANKL1 as it is regulated by vitamin D, while isoform 3 is not.

At the RNA level, we found a marked expression of RANKL, RANK and OPG in the testis from both 10 and 15 weeks old animals (FIG. 2). All the isoforms of RANKL were expressed in the testis. At the protein level, we found expression of RANKL in adult Sertoli cells from two different mice strains. The expression was mixed cytoplasmic and transmembrane. The intensity of the staining varied from very low to normal, but RANKL expression was detectable in the vast majority of Sertoli cells. RANKL appeared to be downregulated in Vdr KO mice, indicating that RANKL also in the testis is regulated by vitamin D. This indicates that the main RANKL isoform present is isoform 1 as RANKL isoform 3 is not regulated by vitamin D in bone and the 10-fold decrease in RANKL following Vdr ablation is substantial.

The specific receptor protein Rank was exclusively expressed in the germ cells with a prominent expression in spermatogonia and spermatocytes. Again, the expression was mixed cytoplasmic and membranous. OPG was expressed mainly in the peritubular cells and the expression was mainly cytoplasmic. At the RNA level TRAf1-6 and NFKβ were also expressed in the mouse gonad indicating that the cells are capable of mediating RANK downstream signalling.

Discussion

Here we show that RANKL, RANK and OPG are expressed in the testis. There appears to be an isoform of RANKL exclusively expressed in Sertoli cells, while RANK is expressed in germ cells and OPG is expressed in peritubular cells. This pattern of expression is conserved from mouse to humans, which indicates that RANKL signalling may be involved in spermatogenesis. It is known that signalling from peritubular and Sertoli cells determines germ cell fate and to our knowledge, this is the first signalling involving peritubular, Sertoli and Germ cells.

The RANKL-system is important for bone homeostasis. The factors involved include the transmembrane RANKL protein in osteoblasts that binds and activates a specific receptor RANK in osteoclasts, which induces differentiation of the immature osteoblasts and results in bone resorption. OPG is an endogenous secreted signalling molecule that binds the ligand domain of RANKL and thus inhibits RANK activation and subsequently osteoclast differentiation and activation, which impairs bone resorption. The American pharmaceutical company Amgen developed a synthetic OPG analog (denosumab) with a long half-life, and EMEA and FDA approved the drug for the treatment of osteoporosis. Denosumab is now used clinically and has very few side effects since RANKL is considered to be expressed only in immune cells, teeth and breast besides bone. FDA or EMEA did not request a male fertility study before the drug could be used clinically because patients with osteoporosis in general are females and of old age.

We have new data showing that one isoform of RANKL is expressed in the male gonad but not in the female counterpart. This RANKL isoform appears to be expressed in Sertoli cells, while the specific receptor RANK is expressed in spermatogonia, and OPG is expressed in peritubular cells. Expression of these proteins is found in both mice and men, and RANKL and RANK are also expressed in Sertoli and germ cells in dysgenetic tubules and pre-cancerous testicular cells (CIS), while CIS tubules have low OPG expression. All the downstream mediators of RANK signalling (TRAF1-6 and NFKβ) are also expressed in the testis from rodents and men, and NFKβ is known to be important for the proliferation-apoptotic switch in the male gonad. Rankl signalling may thus be an important regulator of germ cell proliferation. Inhibition of RANKL in the normal testis may mainly be the Sertoli specific form as it is approachable on the proximal site of the blood-testis barrier, while the presumed cytoplasmic form being expressed in the later stages of spermatogenesis probably is inaccessible for circulating Denosumab. The effect of denosumab cannot be adapted directly from experiments using OPG treatment as Amgen suggested that denosumab unlike OPG does not block TRAIL, which is important for male germ cell apoptosis but only RANKL.

In mice, the expression of RANKL, RANK and OPG is conserved and lessons from Vdr KO mice showed that testicular RANKL is regulated by vitamin D. The RANKL gene has two VDRE and the marked downregulation in Vdr KO mice support the fact that downregulation of RANKL is unlikely to cause a massive decrease in spermatogenesis since these mice have normal testicular histology although they have a modestly impaired fertility, which may be due to RANKL or more likely other causes (see Blomberg Jensen M et al. Characterization of the testicular, epididymal and endocrine phenotypes in the Leuven Vdr-deficient mouse model: targeting estrogen signalling, Mol Cell Endocrinol. 2013 Jul 11; 377(1-2):93-102). Moreover, In bone RANKL isoform 1 is regulated by vitamin D, while isoform 3 is not, and this indicates that the massive downregulation in Vdr mutants indicates that RANKL isoform 1 is the main isoform present.

In conclusion, the presence of RANKL, RANK and OPG in the gonad has never been shown before, and their expression indicates that RANKL signalling through NFKβ may be involved in regulation of proliferation of germ cells. This implies that regulation of the RANKL system may be clinically relevant as it may lower or increase the production of spermatozoa.

Example 3

Introduction

RANKL signalling is important for bone homeostasis, immune system and lactation. RANKL is a transmembrane protein with an extracellular ligand-domain that specifically binds to RANK, a receptor situated in the membrane of the neighboring cell. Binding and activation of RANK induces intracellular signalling often through NFKB activation, which influences cell cycle. Interaction between RANKL and RANK is modulated by OPG secretion from cells in the vicinity as OPG binds to the extracellular domain of RANKL and prevents RANK activation. Therefore, the biological effect of RANKL depends on the presence and abundance of RANKL, RANK and OPG. To make things even more complicated, RANKL exists in three different isoforms 1, 2, 3. One transmembrane form and one cytoplasmic and another secreted form. The different isoforms may not always induce the same effect and the cytoplasmic non-secreted form is in general an inhibitor of RANKL expression. This means that inhibition of RANKL potentially give opposite effects depending on the expression of the specific isoform in the model. The two cell lines TCAM2 and NTERA2 express two different isoforms of RANKL and modulation of this signalling in these germ cell derived cells may indicate the effect of RANKL in the testis.

Denosumab is a man-made specific inhibitor of human RANKL signalling as it does not inhibit the murine RANKL or TRAIL signalling. In monkeys, a 10-fold higher denosumab dose than used regularly did not cause any major testicular histological abnormalities or low sperm motility, but fertility testing was not performed.

Materials and Methods

Human Cell Lines

The EC-derived cell line NTera2 that retain less germ cell characteristics and the seminoma-derived TCam-2 cell line, which retain germ cell characteristics were used in this study. Cells were grown under standard conditions at 37° C. in 5% $CO_2$ atmosphere in DMEM (NTera2) or RPMI 1640 (TCam-2) supplemented with glutamine (58.5 mg/ml), penicillin (100 U/ml) and streptomycin (100 mg/ml) (all Gibco). To investigate the effect on proliferation, RANKL (100 ng/ml), CSF-1 (100 ng/ml), Denosumab (100 ng/ml) were added alone or in combination to the media. DMSO was used as solvent, and all control samples were DMSO treated. Cells were plated in 25-cm² flasks and detached using 0.05% trypsin-EDTA for 5 min at 37° C. One part was centrifuged down and the cell pellet was snap-frozen for RNA purification and cDNA synthesis for RT-PCR. qRT-PCR was performed using specific primers targeting each mRNA.

Representative bands from each primer combination were sequenced for verification (Eurofins MWG GmbH, Germany).

Survival Assay

The survival assay determines the metabolic activity of living cells by measuring the reduction of the oxidized form of resazurin and the concomitant increase in the fluorescent intermediate. Cells were counted manually in a Bürker-Türk counting chamber (Tiefe 0.100 mm, 0.0025 mm$^2$) and $5 \times 10^3$ cells/well were seeded into wells of 96-well plates and incubated overnight before treatment. For co-treatment experiments $1 \times 10^3$ cells/well were plated in 96-well plates, incubated overnight before initial treatment with 100 ng/ml of the selected compound for 20 hours. Negative controls (media only) and positive controls ($1 \times 10^3$ cells in normal media) were included on all plates. Survival of cells was determined using the TOX-8 in vitro toxicity assay (Sigma Aldrich) according to manufacturer's instructions. At the end of treatment resazurin dye from the assay was added to the media followed by 4-6 hours incubation. Plates were then measured on an ELISA microplate reader (Tecan, Sunrise). To calculate percent survival, raw absorbance values were subtracted values from reference wavelength, and the blank samples (media only). Resulting values were averaged (n=8 for each treatment) to generate a final absorbance value. Untreated cells were considered as 100% survival and used to calculate the percent survival of treated cells. Each experiment was repeated at least three times in independent experiments.

Results:

NTera2 cells express one isoform of RANKL that differs from TCAM2 cells. The isoform expressed in the TCAM2 cells is similar to the Sertoli cell specific isoform in Sertoli cell only (SCO), which differs from the one being expressed in the ovary. This isoform may be expressed in the Sertoli cells of normal testis, however, one cannot exclude that normal and SCO only Sertoli cells have different RANKL isoforms. RANK and the downstream signaling machinery are expressed in both cell lines, which mean that they will both be responsive to RANKL treatment (FIG. 1). OPG is exclusively expressed in NTera2 cell, which means that they have a natural inhibitor for RANKL and may adapt to increased exposure and be less sensitive, while TCAM2 does not express OPG.

Figure 4:
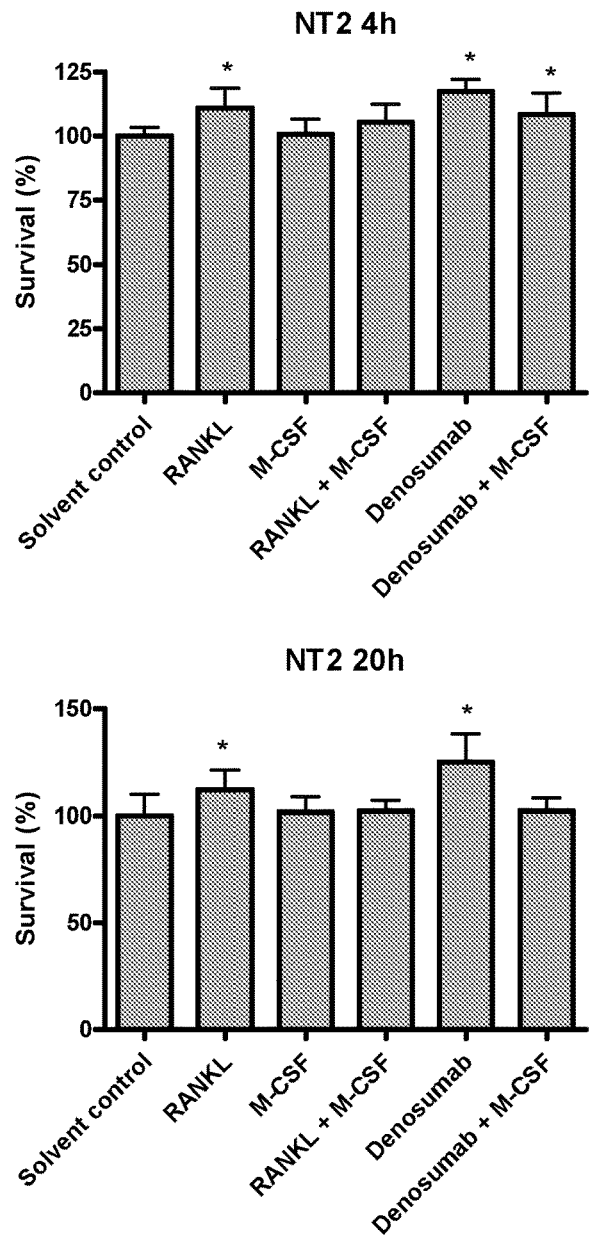
FIG. 4: Survival/proliferation of NT2 cells after treatment for 20 hours, growth in normal media for 14 hours+4 hours with resazurin dye. All treatments are at concentrations of 100 ng/ml. Values are mean±std. (n=8), with * indicating significant difference p<0.05 after t-test.

In NTERA2 cells (FIG. 4) we find an aberrant response since both denosumab and RANKL treatment induce proliferation of the cells after 4 and 20 hours. Denosumab has the strongest effect, but it is not clear why both compounds induce proliferation. One possibility is that denosumab blocks a specific transmenbrane isoform of RANKL on the NTera2cells, which thereby induces proliferation. While exogenous RANKL stimulates RANK as a cytoplasmic isoform and thereby occupies the receptor, which prevents the endogenous transmembrane RANKL to activate RANK on the neighbor cell. The response of the exogenous RANKL may therefore mimic an effect of secreted isoform, which therefore is antagonistic and induces proliferation. The production of OPG may also influence the data, as it may inhibit the endogenous RANKL and this inhibition may be lowered when exogenous RANKL is added.

Figure 5:
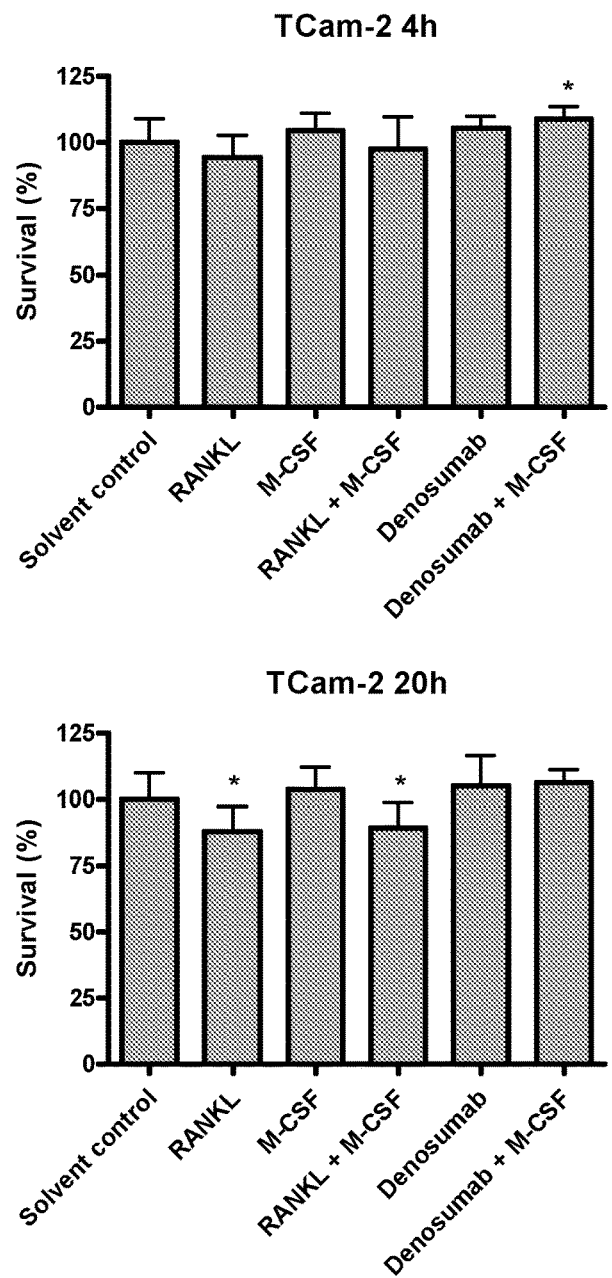
FIG. 5: Survival/proliferation of TCam-2 cells after treatment for 4 and 20 hours, growth in normal media for 10 hours+6,5 hours with resazurin dye. All treatments are at concentrations of 100 ng/ml. Values are mean±std. (n=8), with * indicating significant difference p<0.05 after t-test.

In TCAM2 cells (FIG. 5) another isoform is expressed and here RANKL treatment decreases proliferation as expected, while denosumab again stimulates proliferation although only modestly after 4 hours. All the treatments comprising RANKL lowers proliferation significantly after 20 hours, while denosumab shows insignificant tendencies towards higher proliferation after 20 hours, but it is significant after 4 hours. Another reason to the difference is that, TCAM2 cells does not express OPG and can therefore not abrogate the effect of exogenous RANKL treatment, which may influence their high sensitivity to the treatment.

Discussion

These data show clearly that modulation of the RANKL pathway influence cell survival of cancer cells derived from germ cell tumors. Both RANKL and denosumab treatment induces marked changes in cell survival. Some of the differences in the observed response may be due to the different RANKL isoforms in the two cells. Although the presence of OPG also differs, which obviously influence the results. The change in germ cell proliferation is induced extremely fast and support the fact that both RANKL and denosumab can induce a potent and rapid effect on germ cell survival.

The results from the hanging drop culture of CIS and normal germ cells clearly demonstrate that RANKL signaling between Sertoli and Germ cells is important for germ cell survival and proliferation. RANKL lowers proliferation by inducing apoptosis, while denosumab has the opposite effect. These results may partly be extrapolated to the normal testis, but spermatogonia do not have a strong RANKL expression as most CIS cells, which may influence the results in the normal germ cells. However, the results show clearly that denosumab and RANKL treatment of germ cell in the normal somatic environment regulate germ cell proliferation. In conclusion, by using two different models with different RANKL isoforms, presence or absence of endogenous OPG, different cell lines we have shown that denosumab regulates germ cell proliferation.

Example 4

Ex vivo treatment of human testis with denosumab and RANKL.

Introduction

RANKL signalling is important for bone homeostasis, immune system and lactation. RANKL is a transmembrane protein with an extracellular ligand-domain that specifically binds to RANK, a receptor situated in the membrane of the neighbouring cell. Binding and activation of RANK induces intracellular signalling often through NFKB activation, which influences cell cycle. Interaction between RANKL and RANK is modulated by OPG secretion from cells in the vicinity as OPG binds to the extracellular domain of RANKL and prevents RANK activation. So the biological effect of RANKL depends on the presence and abundance of RANKL, RANK and OPG. To make things even more complicated, RANKL exists in three different isoforms 1, 2, and 3. One transmembrane form and one cytoplasmic and another secreted form. The different isoforms may not always induce the same effect and the cytoplasmic non-secreted form is in general an inhibitor of RANKL expression. This means that inhibition of RANKL potentially give opposite effects depending on the expression of the specific isoform in the model. We have found that RANK is exclusively expressed in germ cells, which therefore are the only cells able to respond to RANKL and denosumab treatment directly. RANKL is expressed in both Sertoli and Germ cells, while OPG is expressed in peritubular cells. We have recently established an organ culture model in which small tissue fragments are cultured in 'hanging drops' of optimised media. This culture approach is applicable for human testis tissue, tissue containing CIS and testicular cancer tumours obtained from orchidectomy specimens of patients with testicular cancer. We have successfully cultured normal testis, tissue with CIS and TGCT for up to 2 weeks without any observed negative changes. This organ culture model allows studies on the mechanisms of RANKL signalling pathways in a dynamic and functional manner, and since the model preserves the integrity of the tissue it has the advantage that the germ cells are sustained within their somatic niche (Sertoli and Peritubular cells) allowing continuous interactions with the somatic cells during treatment experiments. Denosumab is man-made specific inhibitor of human RANKL signalling as it does not inhibit the murine RANKL or TRAIL signalling as the endogenous produced OPG does. In monkeys a 10-fold higher denosumab dose than used regularly did not cause any major testicular histological abnormalities or low sperm motility, but fertility testing was not performed.

Materials and Methods

Human Tissue Sample Collection and Preparation

Patients were recruited from the Andrology Clinic of the Department of Growth and Reproduction at Copenhagen University Hospital (Denmark) in accordance with the Helsinki Declaration, and following approval from the local ethics committee (permit nr. H-1-2012-007). All participants gave informed consent before orchidectomy for treatment of testicular cancer. The orchidectomy specimens were transported immediately after surgical removal to the Pathology Department and were divided into tumour and macroscopically normal areas. The majority of the tissue was assigned for diagnostic analysis, with the remainder for research. The sample portions assigned for research were placed immediately in media (see below) and transported to the laboratory. Within 2 h of surgical removal, the specimens were cut into ~1 mm3 pieces (an average seminiferous tubule is 150 μm in diameter) and placed into hanging drop cultures in media containing DMEM F12, penicillin (100 U/ml-1), streptomycin (100 mg/ml-1), insulin, transferrin and selenium (×1) with either 10% fetal bovine serum (FBS) or 0.1% bovine serum albumin (BSA). In the initial phase of culture condition optimisation, several different basic media were tested, including DMEM, RPMI-1640 and MEMα, but no apparent differences in survival or tissue morphology were observed (data not shown). All cell media and supplements were from Gibco (Naerum, Denmark), except BSA (Sigma-Aldrich, Broendby, Denmark). To set-up the cultures, 30 μl drops of medium were prepared on the lid of a Petri-dish (NUNC cell culture Petri-dish). Individual tissue pieces were placed into each drop, and then the dish was carefully inverted to keep the drops intact with the tissue suspended. DPBS (10 ml) was added to the bottom of the dish to prevent dehydration. Tissues were cultured at 34° C. in 5% CO2 for up to 14 days, with media changed every 48 h. The experimental set-up included at least three replicates of tissue pieces cut from the same original tissue piece for each of the following: fixation, RNA purification and survival assay. When the culture period was completed, samples were collected into 4% paraformaldehyde (PFA) fixative (30 min at room temperature, 4° C. overnight) followed by paraffin embedding for histological analysis and immunohistochemistry, placed in RNAlater (Ambion, Austin, Tex., USA) for RNA purification and real-time PCR analyses or set-up in a survival assay.

Survival Assay

To evaluate whether the tissue pieces contained living cells, a survival assay was used to determine total metabolic activity using the TOX-8 in vitro toxicity assay (Sigma-Aldrich), according to the manufacturer's instructions. In brief, tissue pieces were transferred to a 96-well dish with 90 μl media and 10 μl resazurin dye (Sigma-Aldrich) and incubated for 5 h at 34° C. together with negative experimental controls (media+resazurin dye, without tissue) that were included on all plates. The reduction of the oxidised form of resazurin (blue) and the concomitant increase in the fluorescent intermediate (red) were then measured on an ELISA microplate reader (Tecan Sunrise, Männedorf, Switzerland) according to the manufacturer's instructions (Sigma-Aldrich).

Immunohistochemistry

In brief, paraffin sections were deparaffinised and rehydrated. Antigen retrieval was accomplished by microwaving the sections for 15 min in retrieval buffer. Sections were then incubated with 2% non-immune goat serum (Zymed Histostain kit, San Francisco, Calif., USA) or 0.5% milk powder diluted in Tris buffered saline (TBS) to minimise cross-reactivity. Primary antibodies, dilutions and retrieval buffers. After 16 h of incubation at 4° C. and 1 h at room temperature, the sections were incubated with biotinylated goat anti-rabbit IgG (Zymed Histostain kit) or biotinylated goat anti-mouse IgG (1:400), before a peroxidase-conjugated streptavidin complex (Zymed Histostain kit) was used as a tertiary layer. Visualisation was performed with amino ethyl carbasole (AEC) (Zymed Histostain kit) yielding a deep red colour. Between incubation steps, the slides were washed with TBS. For negative controls, serial sections were processed, with the primary antibody replaced by the dilution buffer alone. None of the control slides showed any staining. Counterstaining was performed with Mayer's haematoxylin. Serial sections were used to test for expression of PLAP (signal detected in CIS and seminoma cells), KI-67, BrdU incorporation, cleaved caspase, KIT and AP2γ. Two independent investigators evaluated all staining. All sections were investigated manually on a Nikon Microphot-FXA microscope (Tokyo, Japan) and were then scanned on a NanoZoomer 2.0 HT (Hamamatsu Photonics, Herrsching am Ammersee, Germany) and analysed using the software NDPview version 1.2.36 (Hamamatsu Photonics). To evaluate the immunohistochemical (IHC) stainings in a more quantitative manner, the percentages of KI-67-, BrdU-, KIT- and AP2γ-stained cells were determined by cell counting. The proliferation markers KI-67 and BrdU were expressed only in normal and malignant germ cells, with a weakly KI-67-stained Sertoli cell observed only very rarely. In normal testis samples with complete spermatogenesis, we counted only spermatogonia and spermatocytes; in samples containing CIS, we determined also the proportion of stained CIS cells. For all quantifications (KI-67, BrdU, KIT and AP2γ), a minimum 3.5 mm2 tissue were evaluated by two different investigators in each of three tissue fragments per treatment from each patient. Tissue pieces from at least three different patients were included for vehicle, rankl and denosumab treatment. Both positive and negative cells were counted to calculate the percentage of stained cells.

Proliferation Assay

A BrdU incorporation assay was used to determine the presence of proliferating germ cells just before the end of the culture period. BrdU labelling reagent (Invitrogen, Camarillo, Calif., USA) was diluted 1:100 in media and tissue pieces were set up as hanging drop cultures in BrdU containing media for 3 h. Tissue pieces were then washed twice in PBS for 5 min followed by fixation and paraffin embedding as described above. BrdU was visualised by immunohistochemistry using a BrdU antibody as described in the Immunohistochemistry section, and positively stained cells were considered as proliferating.

Results

The overall morphology of tissue with areas containing full spermatogenesis termed normal testis tissue (NT) and testis tissue with tubules containing CIS cells was maintained for up to 14 days in hanging drop tissue cultures. Staining of NT tissue with Haematoxylin & Eosin (HE) demonstrated the presence of all germ cell types, and staining with the CIS marker PLAP confirmed whether CIS cells were present. After 7-10 days of culture, a loss of more differentiated germ cells, particularly the post-meiotic spermatids, was observed in tissue from some patients, but this was not a consistent finding. In tissue containing tubules with CIS cells, staining with HE and PLAP demonstrated that the tubules contained predominantly CIS cells (positive for PLAP) and Sertoli cells and that morphology of the tissue was preserved during culture for up to 14 days.

Two measures of cell proliferation were applied in this study: IHC staining with KI-67 and a BrdU incorporation assay. To directly compare the proliferation measures, KI-67 and BrdU staining's were performed on serial sections of tissue pieces. In general, a significantly ($P<0.05$) higher number of labelled cells was found by detection of KI-67 compared with BrdU. These data also indicate that BrdU incorporation, followed by antibody detection, is a more specific marker for cell proliferation than the KI-67 staining. This is expected, as BrdU is incorporated into DNA as a thymidine analogue only during S phase of the cell cycle in the last 3 h of the culture period. In contrast, KI-67 is expressed in all phases of the cell cycle, except during G0/G1 arrest, and the following results will only be presented with BrdU incorporation.

Figure 6:
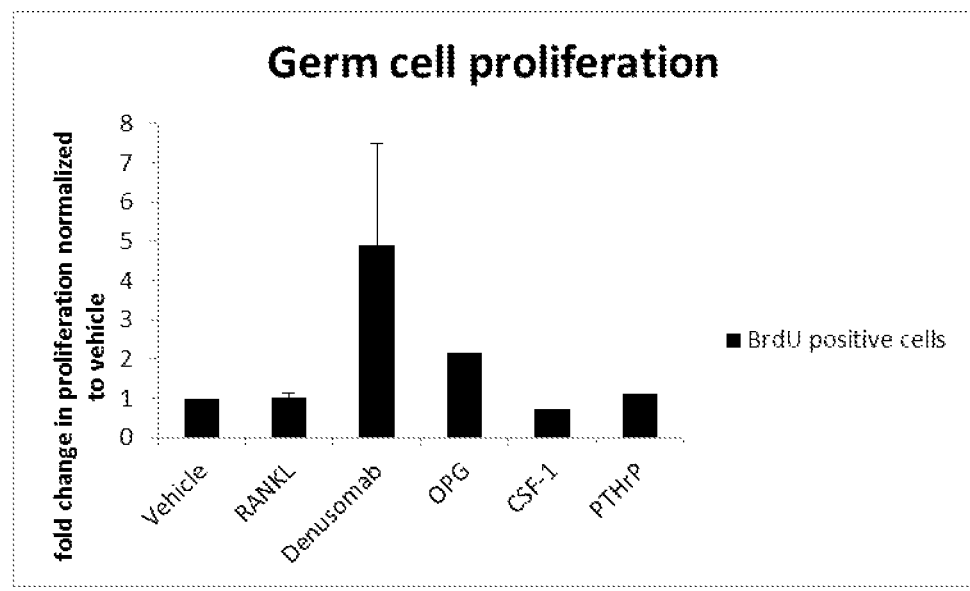
FIG. 6 shows germ cell proliferation in human ex vivo model. Germ cell proliferation was assessed by BrdU incorporation following 48 hours treatment of human testis specimens (N=3) with vehicle (DMSO), 100 ng/ml RANKL or 100 ng/ml denosumab and also compared with one testis treated with 50 ng/ml OPG, 100 ng/ml CSF-1 and 100 ng/ml PTHrP. Data presented as mean change in proliferation+sem and data normalised to vehicle treated samles.

Results from treatment of human testis specimens in hanging drop culture revealed a marked change in germ cell proliferation. In total, we used testis from four men, but only three of the men had testicular tissue present in the specimens. The size of each specimen used for each treatment was on average 5.92 mm2. Each treatment lasted for 48 hours and we used two control specimens from all testis to avoid bias from different histology in the serial sections. Using this approach, we ensure that the germ cells are kept in their normal intratubular niche in contact with the Sertoli cells. This means that the cells are exposed to the Sertoli specific form of RANKL. Two specimens contained both normal tissue and premalignant CIS cells, while one did not contain normal spermatogenesis but the only germ cells found were CIS cells. Treatment with denosumab and OPG increased proliferation of germ cells markedly, while RANKL and other drugs known to influence RANKL signaling in bone CSF-1 and PTHrP do not have a similar effect treatment was unable to induce a significant change in germ cell proliferation as assessed by BrdU incorporation (FIG. 6). Denosumab induced an increase in the fraction of proliferation germ cells by more than 70% in two of the patients, while denosumab induced an 11-fold increase in the last patient who had a very severe testicular phenotype histologically. The positive effect of denosumab was comparable with the effect of OPG-FC, which besides inhibiting RANKL also blocks TRAIL.

Figure 7:
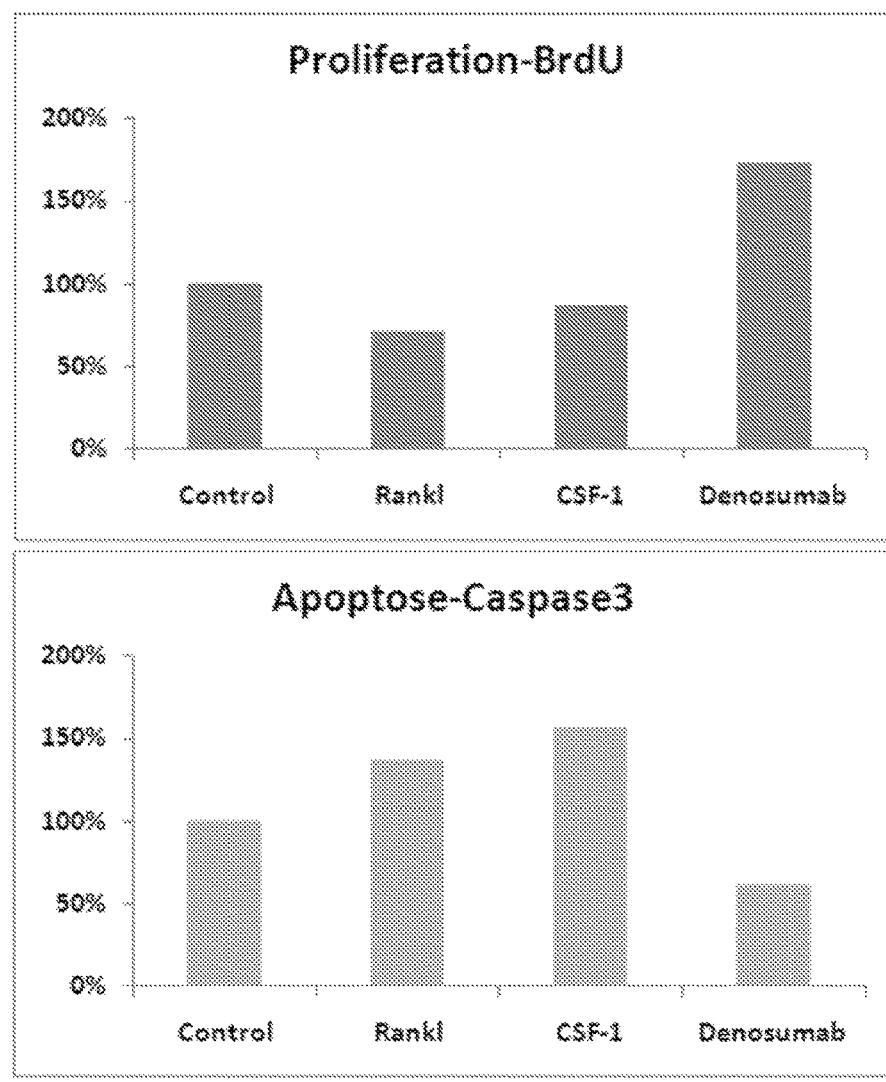
FIG. 7 shows the effect on proliferation (top) and apoptosis (buttom) of treatment with RANKL, CSF-1, denosumab and control in an ex vivo human testicular model containing Carcinoma in situ cells intratubularly. The mean number of germ cells expressing BrdU or Caspase 3 has been counted to compare the effect between the treatments.

CIS cells resemble fetal germ cells and differ from spermatogonia because some express RANKL themselves. However, they are situated in the correct niche as spermatogonia and respond in a similar manner as the normal germ cells, since RANKL decreases proliferation by inducing Caspase dependent apoptosis, while denosumab increases proliferation by inhibiting Caspase dependent apoptosis (FIG. 7). The effect is rapid and marked and the opposite effect of exogenous RANKL treatment is a strong indicator of a reproducible effect of treatment in vivo because the cells are exposed in their natural environment.

Discussion

Without being bound by theory, these data show clearly that modulation of the RANKL pathway influence germ cell survival and proliferation. Both RANKL and denosumab treatment induces marked changes in cell survival. Some of the differences in the observed response may be due to the different RANKL isoforms present in the testis. The changes in germ cell proliferation are induced extremely fast as expected and support the fact that both RANKL and denosumab can induce a potent and rapid effect on germ cell survival.

The results from the hanging drop culture of CIS and normal germ cells clearly demonstrate that RANKL signaling between Sertoli and Germ cells is important for germ cell survival and proliferation. The results show clearly that denosumab and RANKL treatment of germ cell in the normal somatic environment regulate germ cell proliferation, while other drugs known to influence RANKL signaling in bone CSF-1 and PTHrP do not have a similar effect (FIG. 6).

In conclusion, by using germ cells situated in their normal environmental niece, we have shown that denosumab and OPG induce germ cell proliferation.

Example 5

In vivo effects of inhibition of testicular RANKL inhibition by infusing human OPG-FC, RANKL, as well as vehicle to mice for a period of 14 days.

Mice are recognized models for the study of pharmacodynamics and pharmacokinetic effects of medical treatment. Unfortunately, we were unable to test the effect of denosumab because denosumab is unable to block mouse RANKL. Instead we used human OPG, which effectively block the effect of mouse RANKL and may act in a similar fashion as denosumab as previously shown in example 4.

Material and Methods

Animals

C57BL/6J mice, 15 males, 7-8 weeks of age from Taconic Europe A/S. The mice were caged in European standard cages type II. Bedding Jeluxyl HW 300/500 (Jelu, J.Ehrler GmbH & Co KG, Ludwigsm Ohle, D-73494 Rosenberg, Germany). The bedding was changed once a week in a laminar flow unit. The air was exchanged approximately 12 times per hour in the stable. Temperature was 20° C. to 24° C., and controlled via the ambient ventilation system. Light cycle was 12-hour dark and 12-hour light (lights on 06.00). Diet Altromin 1324, produced by Altromin, Im Seelenkamp 20, 32791 Lage, Germany. Water was UV-sterilized and water bottles was refilled when necessary during acclimatization and experiment. Diet and was administered ad libitum.

The following test articles were used

| Gr. No. | Test article 1 (ID) | Amount, received | Storage | Special |
|---|---|---|---|---|
| 1 | OPG-FC (cyt-177-c) | 2 mg | −20 C. | Powder(compound) |
| 2 | RANKL (cyt-692-b) | 200 µl (20 µg/40 µl) | −20 C. | Liquid |
| 3 | Vehicle (PBS) | — | Room temp | Liquid |

The following dose solutions were used:

| Gr. No. | Test article 1 (ID) | Conc | Dose Vol | Dose | Route |
|---|---|---|---|---|---|
| 1 | OPG-FC (cyt-177-c) | 0.2 mg/ml | 5 ml/kg | 1 mg/kg | i.p |
| 2 | RANKL (cyt-692-b) | 8 µg/ml | 5 ml/kg | 40 µg/kg | i.p |
| 3 | Vehicle | — | 0.1 ml/mice | — | i.p |

Experimental Design

Fifteen (15) mice (Gr. 1-3) was randomized into 3 groups of 5 animals. Treatment of the mice take place as indicated in the table below. The mice was monitored for abnormal clinical symptoms. Body weights will be determined before each round of dosing. The mice was terminated after 14 days of dosing. At termination the mice was euthanized by cervical dislocation. Three hundred (300) µl blood was collected from each animal and 100-150 µl serum will be prepared. Kidneys and testicles will be dissected free and weighed. The samples were preserved as follows: Kidney samples: One Snap frozen and one in buffered formalin or PFA Testis samples: One testis in formalin or PFA, ½ testis in bouins fixative and ½ testis snap frozen. Epididymis snap frozen.

| Gr. No. | n | Test article 1 (ID) | Dose | Route | Frequency | Special |
|---|---|---|---|---|---|---|
| 1 | 5 | OPG-FC (cyt-177-c) | 1 mg/kg | i.p | 2 × weekly | |
| 2 | 5 | RANKL (cyt-692-b) | 40 µg/kg | i.p | 3 × weekly | |
| 3 | 5 | Vehicle | — | i.p | 3 × weekly | |

Clinical Observations

All animals are inspected on a daily basis for their general condition. Any clinical signs or behavioral abnormalities are recorded.

Caudal epididymides were minced in 1 ml PBS 1× and the number of cells released counted after 1 hour. The total sperm count was assessed in the final suspension by using a hemocytometer.

Humane End-points and Premature Termination

Any animals showing clinical signs of more than mild pain or moderate distress will be humanely euthanized. This includes animals exhibiting clinical signs that exceed the limits of the humane end-points. If an animal is found dead or is euthanized prematurely during the study then the time of death will be recorded as precisely as possible. The body weight will be measured before euthanasia or at the time of finding of the dead animal. If possible, a post mortem examination will be conducted on the animal. The animal external and internal appearance and the pivotal organs will be inspected and described in accordance to the 'Post Mortem Examination Schedule' and the organ weights will be recorded. The pivotal organs will be preserved in formalin in one vial per animal. At the termination of the control group, animals then identical post mortem examinations will be conducted on the control group animals. This is to make further investigation possible.

Results

Body Weight and Distress

There was no major difference in body weight following treatment with Vehicle, RANKL or OPG. The animals showed no sign of distress.

Testis Size and Epididymis

Figure 8:
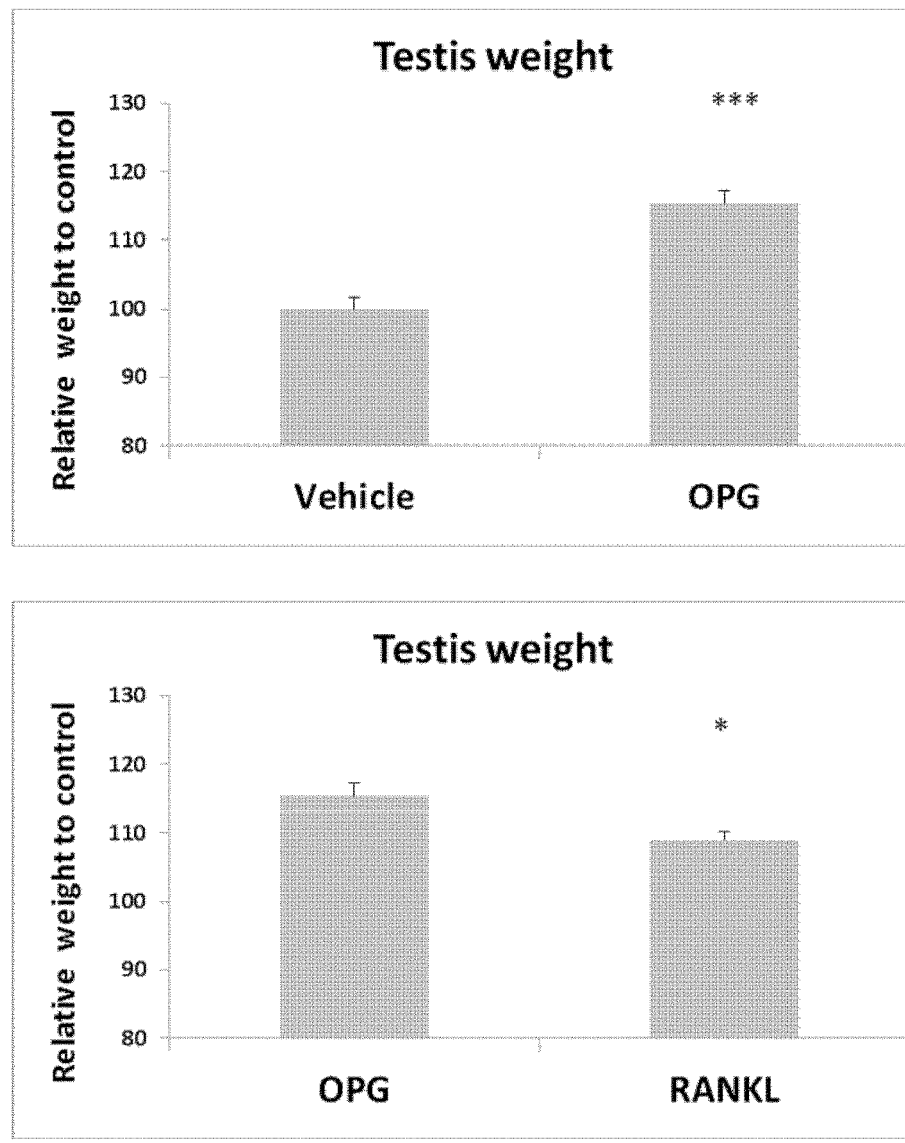
FIG. 8 shows total testes weight in mice treated with vehicle, OPG or RANKL. Testis weight was assessed after 14 days treatment of 15 mice (5 mice randomized to each treatment:vehicle RANKL or OPG). Data presented as mean+sem and data normalised to vehicle treated samles. * mark p<0.05 and *** p<0.001.
Figure 9:
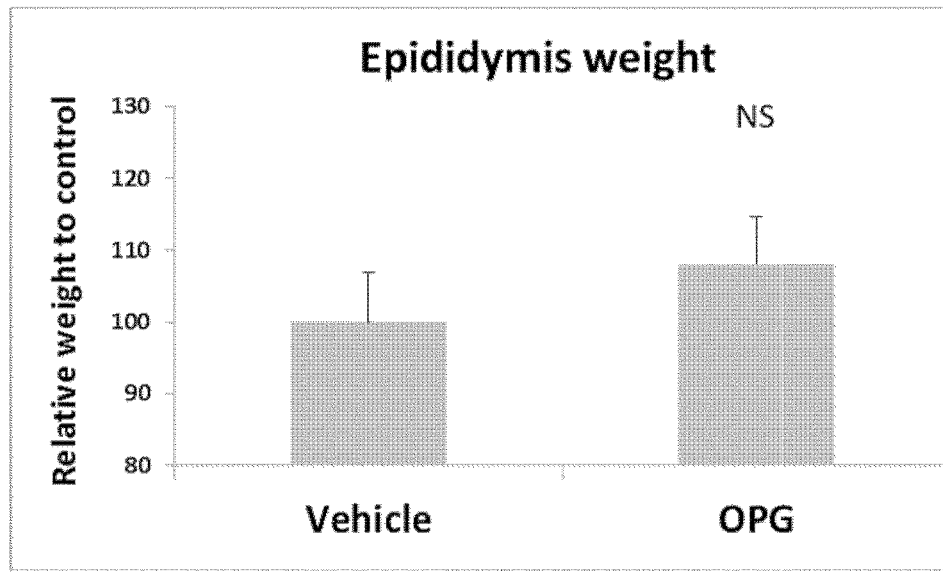
FIG. 9 shows total epididymal weight in mice treated with vehicle, OPG or RANKL. Testis weight was assessed after 14 days treatment of 15 mice (5 mice randomized to each treatment:vehicle RANKL or OPG). Data presented as mean+sem and data normalised to vehicle treated samles. NS mark p>0.05 and *p<0.05.
Figure 9:
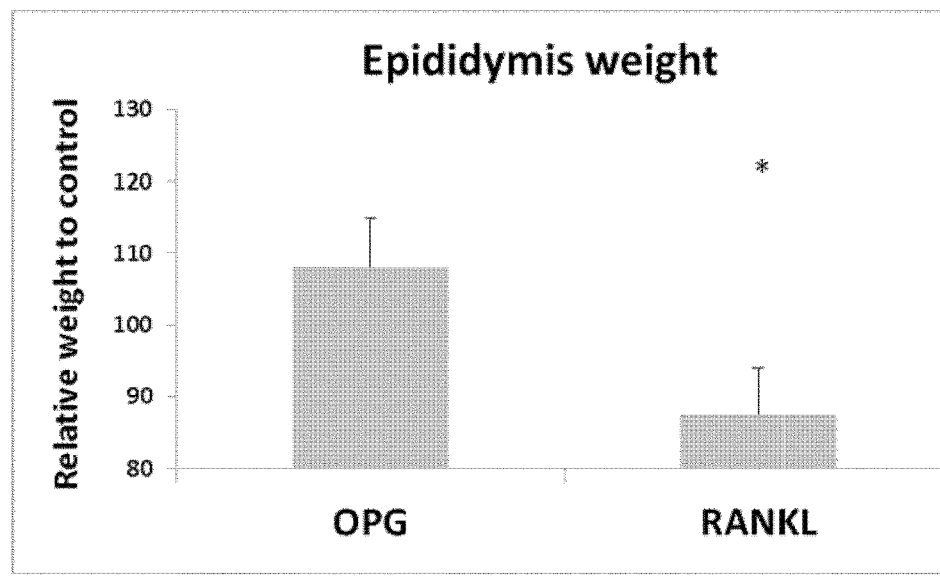
Figure 10:
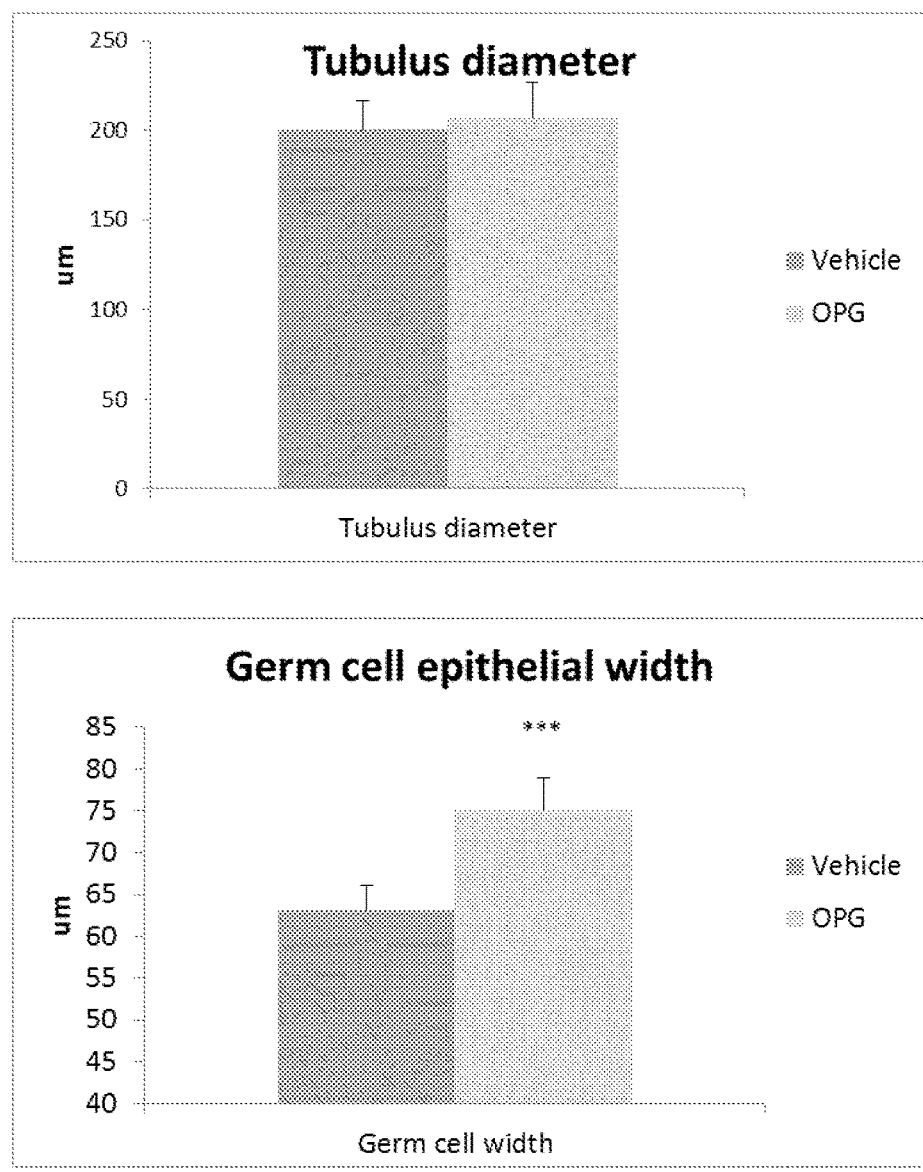
FIG. 10 shows testicular morphometry in 10 week old mice. Testis from 10 old mice were fixed in Bouin and Seminiferous tubules with germ cell epithelia (stage 6-12) were assessed (N=3 from each treatment arm).) Comparison of tubular diameter (top) and germ cell epithial width (buttom) in mice treated with vehicle or OPG for 14 days. Bars indicate mean±s.e.m.

A comprehensive evaluation of male fertility potential was not performed, but the weight of the reproductive organs (testis and epididymis) was significantly higher in OPG treated mice compared with vehicle and RANKL treated mice respectively (FIGS. 8 and 9). In addition, more tubules appeared wider in OPG treated mice compared with RANKL and vehicle treated 10 weeks old mice (FIG. 10, top), and, germ cell epithelial width was significantly wider independent of the stage of spermatogenesis in the OPG treated mice (FIG. 10, buttom). The increased germ cells in the OPG treated mice may explain the difference in epididymal weight, which could be caused by a higher number of accumulating spermatozoa in the OPG-treated mice compared with RANKL treated mice.

Sperm Count

Figure 11:
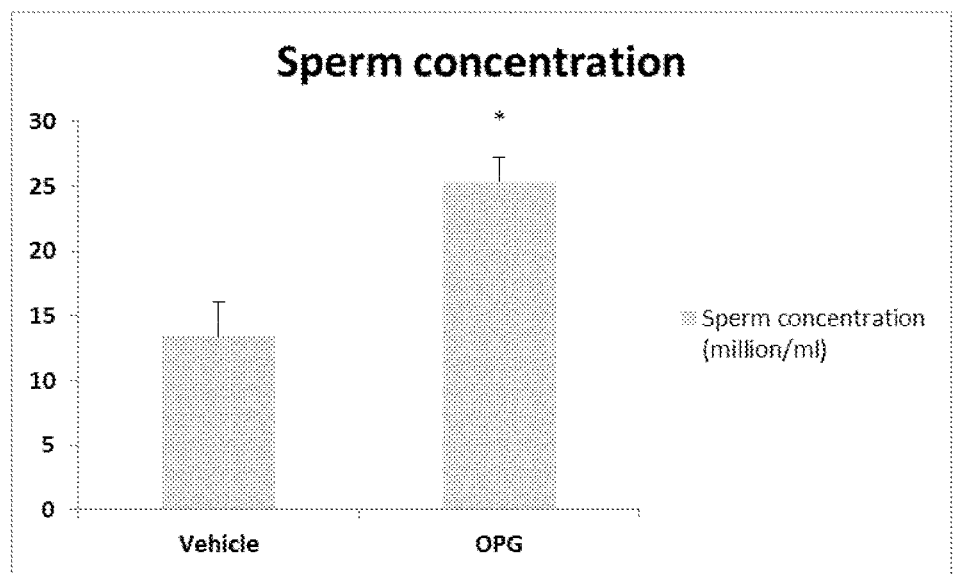
FIG. 11 shows sperm count in mice treated with vehicle or OPG. Sperm count was assessed following miching of cauda epididymis in 1 ml PBS was (5 mice randomized to each treatment vehicle or OPG). Data presented as mean+sem. * mark p<0.05.

To verify this, we released spermtatozoa from cauda epididymis from both vehicle and OPG treated mice since these spermatozoa are fully matured and ready for ejaculation and therefore is an indirect marker of their fertility potential. We found a marked difference in sperm concentration. OPG treated mice had an significant higher (p=0.02) average sperm concentration of 25. 3 million per ml compared with vehicle treated mice 13.4 million per ml (FIG. 11). The marked difference in sperm count between OPG and vehicle treated mice is in line with the significant differences in the organ weight of testis and epididymis and the width of the germ cell layer in the testis, which strongly support that OPG treated mice have a better semen quality and as a result better fertility potential.

Discussion

Without being bound by theory, in this comprehensive study of the reproductive organs of mice treated with exogenous RANKL, OPG or vehicle for two weeks, we showed that inhibition of RANKL signaling by using OPG treatment lead to significant changes in the weight and histology of the testis and epididymis. This is in line with the previous results presented above documenting that RANKL is expressed in the testis. In addition, the above in vitro and ex vivo data indicate that inhibition of RANKL with denosumab or OPG results in germ cell proliferation. In accordance, the germ cell layer in OPG treated mice is significantly wider compared with vehicle and RANKL treated mice indicating that the increase in testis weight is due to increased number of germ cells. Especially epidididymis weight is significantly different between RANKL and OPG treated mice, which may be due to lower sperm number situated in the epididymis of RANKL treated mice compared with OPG treated mice. Again, these results are in accordance with the results showing that sperm counts were significantly higher in OPG treated mice compared with vehicle treated mice, which strongly support that OPG treatment improves fertility potential in mice.

In conclusion, The marked difference in sperm count between OPG and vehicle treated mice is in line with the significant differences in the organ weight of testis and epididymis and the width of the germ cell layer in the testis, which strongly support that OPG treated mice have a better semen quality and as a result better fertility potential.

Thus, evidence is provided showing the presence of RANKL, RANK and OPG in murine testis may be of clinical importance and exogenous treatment with OPG and/or denosumab may be used as a fertility improving drug.

The invention claimed is:

1. A method of increasing sperm production in a male subject, comprising:
   selecting a male subject with spermatogenic failure; and
   administering to said male subject a therapeutically effective amount of a composition comprising Denosumab or an antigen binding domain thereof, or osteoprotegerin (OPG).

2. The method according to claim 1, wherein the composition comprises Denosumab.

3. The method according to claim 1, wherein the composition comprises a Denosumab antigen binding domain.

4. The method according to claim 1, wherein said method includes treating oligospermia.

5. The method according to claim 1, wherein said method includes treating azoospermia.

6. The method according to claim 1, wherein said composition is administered intravenously or subcutaneously.

7. The method according to claim 1, wherein said composition is administered subcutaneously.

8. The method according to claim 1, wherein said composition, is administered intra-intesticularly or in the genital region.

9. The method according to claim 1, wherein said composition, is administered in the scrotal region.

10. The method according to claim 1, wherein the composition is administered to a male subject who does not suffer from testicular cancer at any stage, which is detectable by histological analysis of a tissue sample of the testis from said subject.

11. The method according to claim 1, wherein said method includes treating oligospermia or azoospermia in male mammals, or increasing sperm production in male mammals.

12. The method according to claim 1, wherein said composition is in a pharmaceutical composition.

13. A method of treating oligospermia or azoospermia in a male mammal, or of increasing sperm production in the male mammal, said method comprising administering a therapeutically effective amount of OPG (osteoprotegerin) or a fusion protein comprising OPG to the male mammal, wherein the male mammal has spermatogenic failure.

14. A method of treating oligospermia or azoospermia in a male mammal, or of increasing sperm production in the male mammal, said method comprising administering a therapeutically effective amount of Denosumab to the male mammal, wherein the male mammal has spermatogenic failure.

* * * * *